" 
US009630992B2

(12) United States Patent
Lambris et al.

(10) Patent No.: US 9,630,992 B2
(45) Date of Patent: *Apr. 25, 2017

(54) COMPSTATIN ANALOGS WITH IMPROVED PHARMACOKINETIC PROPERTIES

(75) Inventors: John D. Lambris, Philadelphia, PA (US); Hongchang Qu, Drexel Hill, PA (US); Daniel Ricklin, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 3 days.

This patent is subject to a terminal disclaimer.

(21) Appl. No.: 14/343,003

(22) PCT Filed: Sep. 7, 2012

(86) PCT No.: PCT/US2012/054180
§ 371 (c)(1),
(2), (4) Date: Jul. 16, 2014

(87) PCT Pub. No.: WO2013/036778
PCT Pub. Date: Mar. 14, 2013

(65) Prior Publication Data
US 2015/0158915 A1 Jun. 11, 2015

Related U.S. Application Data

(60) Provisional application No. 61/531,919, filed on Sep. 7, 2011, provisional application No. 61/651,204, filed on May 24, 2012.

(51) Int. Cl.
*A61K 38/10* (2006.01)
*C07K 7/08* (2006.01)
*C07K 7/64* (2006.01)
*A61K 38/12* (2006.01)
*A61K 45/06* (2006.01)
*A61K 38/00* (2006.01)

(52) U.S. Cl.
CPC ............... *C07K 7/64* (2013.01); *A61K 38/10* (2013.01); *A61K 38/12* (2013.01); *A61K 45/06* (2013.01); *C07K 7/08* (2013.01); *A61K 38/00* (2013.01)

(58) Field of Classification Search
CPC .................. A61K 38/10; C07K 7/08
See application file for complete search history.

(56) References Cited

U.S. PATENT DOCUMENTS

| 4,299,838 | A | 11/1981 | Durlach |
| 4,576,750 | A | 3/1986 | Pitzenberger |
| 4,870,097 | A | 9/1989 | Makovec et al. |
| 5,167,960 | A | 12/1992 | Ito et al. |
| 5,256,642 | A | 10/1993 | Fearon et al. |
| 5,776,970 | A | 7/1998 | Shechter et al. |
| 6,169,057 | B1 | 1/2001 | Lovatt |
| 6,214,790 | B1 | 4/2001 | Richelson et al. |
| 6,319,897 | B1 | 11/2001 | Lambris et al. |
| 7,989,589 | B2* | 8/2011 | Lambris ................. A61K 38/10 530/327 |
| 8,946,145 | B2* | 2/2015 | Lambris ................. C07K 7/08 514/2.9 |
| 2001/0023066 | A1 | 9/2001 | Kinders et al. |
| 2013/0344082 | A1* | 12/2013 | Lambris ................. A61K 38/12 424/158.1 |
| 2014/0371133 | A1* | 12/2014 | Francois ................. A61K 38/12 514/1.7 |
| 2015/0110766 | A1* | 4/2015 | Lambris ................. C07K 14/472 424/94.5 |
| 2016/0067357 | A1* | 3/2016 | Francois ................. C12Q 1/37 424/9.6 |

FOREIGN PATENT DOCUMENTS

| WO | WO 91/16345 A1 | 10/1991 |
| WO | WO 95/23512 A1 | 8/1995 |
| WO | WO 99/13899 A1 | 3/1999 |
| WO | WO 2004/026328 A1 | 4/2004 |
| WO | WO 2007/044668 A1 | 4/2007 |
| WO | WO 2007/062249 A2 | 5/2007 |
| WO | WO 2008/153963 A1 | 12/2008 |
| WO | WO 2010/127336 A1 | 11/2010 |
| WO | WO 2010/135717 A2 | 11/2010 |
| WO | WO 2011/163394 A2 | 12/2011 |
| WO | WO 2012/040259 A2 | 3/2012 |

OTHER PUBLICATIONS

Bellows et al. New Compstatin Variants through Two De Novo Protein Design Frameworks. Biophysical Journal. May 2010, vol. 98, pp. 2337-2346.*
Qu et al. New analogs of the clinical complement inhibitor compstatin with subnanomolar affinity and enhanced pharmacokinetic properties. Immunobiology. 2013, vol. 218, pp. 496-505 (available online Jun. 17, 2012).*
Qu et al. Development of Compstatin Derivative-Albumin Binding Peptide Chimeras for Prolonged Plasma Half-Life. Breaking Away: Proceedings of the 21$^{st}$ American Peptide Symposium, Michal Lebl (ed.). 2009, pp. 219-220.*
Lopez de Victoria et al. A New Generation of Potent Complement Inhibitors of the Compstatin Family. Chemical Biology & Drug Design. Apr. 26, 2011. vol. 77, No. 6, pp. 431-440.*
Babitzke et al., "Structural features of L-tryptophan required for activation of TRAP, the *trp* RNA-binding attenuation protein of *Bacillus subtilis*," *J. Biol. Chem.*, vol. 270, pp. 12452-12456 (1995).
Beene et al., "Cation-π interactions in ligand recognition by serotonergic (5-HT$_{3A}$) and nicotinic acetylcholine receptors: the anomalous binding properties of nicotine," *Biochemistry*, vol. 41, pp. 10262-10269 (2002).

(Continued)

*Primary Examiner* — Jeffrey E Russel
(74) *Attorney, Agent, or Firm* — Potter Anderson and Corroon LLP

(57) ABSTRACT

Compounds comprising peptides capable of binding C3 protein and inhibiting complement activation are disclosed. The compounds comprise compstatin analogs in which the N-terminus contains an added or substituted component that improves (1) the peptide's binding affinity to C3 or its fragments, (2) the peptide's solubility in aqueous liquids, (3) the peptide's plasma stability, (4) the peptide's in vivo retention and/or (5) the peptide's bioavailability, as compared with an unmodified compstatin peptide under equivalent conditions. Pharmaceutical compositions and methods of using the compounds are also disclosed.

20 Claims, 7 Drawing Sheets

(56) References Cited

OTHER PUBLICATIONS

Beeley, N., "Pedidomimetrics and small-molecular drug design: towards improved bioavailability and in vivo stability", *Trends Biotechnol.*, vol. 12, pp. 213-216 (1994).

Biron et al., "Optimized selective N-methylation of peptides on solid support", *J. Peptide Sci.*, vol. 12, pp. 213-219 (2006).

Bowie et al., "Deciphering the Message in Protein Sequences: Tolerance to Amino Acid Substitutions", *Science*, vol. 247, pp. 1306-1310 (1990).

Brooks et al., "CHARMM: A Program for Macromolecular Energy, Minimization, and Dynamics Calculations", *J. Comput. Chem.*, vol. 4, pp. 187-217 (1983).

Chatterjee et al., "N-Methylation of Peptides: A New Perspective in Medicinal Chemistry", *Acc. Chem. Res.*, vol. 41, pp. 1331-1342 (2008).

Chiu et al., "Development of a New Pharmacophore Model That Discriminates Active Compstatin Analogs," *Chem. Biol. Drug Des.*, vol. 72, pp. 249-256 (2008).

Coleman et al., "Age-related macular degeneration", *Lancet*, vol. 372, pp. 1835-1845 (2008).

Darden et al., "Particle Mesh Ewald-an N.Log(N) method for Ewald sums in large systems", *J. Chem. Phys.*, vol. 98, pp. 10089-10092 (1993).

Dennis et al., "Albumin binding as a general strategy for improving the pharmacokinetics of proteins," *J. Biol Chem.*, vol. 277, pp. 35035-35043 (2002).

Feller et al., "Constant pressure molecular dynamics simulation: The Langevin piston method", *J. Chem. Phys.*, vol. 103, pp. 4613-4621 (1995).

Fiane et al., "Compstatin, a peptide inhibitor of C3, prolongs survival of ex vivo perfused pig xenografts,"*Xenotransplantation*, vol. 6, pp. 52-65 (1999).

Fiane et al., "Prolongation of ex vivo-perfused pig xenograft survival by the complement inhibitor Compstatin," *Transplant Proc.*, vol. 31, pp. 934-935 (1999).

Fiane, et al., "Modulation of Fluid-Phase Complement Activation Inhibits Hyperacute Rejection in a Porcine-to-Human Xenograft Model", *Transplantation Proceedings*, vol. 32, pp. 899-900 (2000).

Furlong, et al., "C3 activation is inhibited by analogs of compstatin but not by serine protease inhibitors or peptidyl α-ketoheterocycles", *Immunopharmacology*, vol. 48, pp. 199-212 (2000).

Holers, "The complement system as a therapeutic target in autoimmunity", *Clin. Immunol.*, vol. 107, pp. 140-151 (2003).

Hruby, V.J., "Conformational and topographical considerations in the design of biologically active peptides", *Biopolymers*, vol. 33, pp. 1073-1082 (1993).

Humphrey et al., "VMD: visual molecular dynamics", *J. Mol. Graphics*, vol. 14, pp. 33-38 (1996).

Janssen et al.,"Structure of compstatin in complex with complement component C3c reveals a new mechanism of complement inhibition," *J. Biol. Chem.*, vol. 282, pp. 29241-29247 (2007).

Jorgensen et al., "Comparison of simple potential functions for simulating liquid water", *J. Chem. Phys.*, vol. 79, pp. 926-935 (1983).

Kalli, et al., "Therapeutic uses of recombinant complement protein inhibitors", *Springer Seminars in Immunopathology*, vol. 15, pp. 417-431 (1994).

Katragadda, M., et al., "Thermodynamic studies on the interaction of the third complement component and its inhibitor, compstatin," *J. Biol. Chem.*, vol. 279, pp. 54987-54995 (2004).

Katragadda et al., "Hydrophobic effect and hydrogen bonds account for the improved activity of a complement inhibitor, compstatin," *J. Med. Chem.*, vol. 49, pp. 4616-4622 (2006).

Katragadda et al., "Expression of compstatin in *Escherichia coli*: Incorporation of unnatural amino acids enhances its activity," *Protein Expr. Purif.*, vol. 47, pp. 289-295 (2006).

Katragadda, M., et al., "Structure-activity-based design of potent compstatin analogs," *Mol. Immunol.*, vol. 44, p. 192 (2007) [Abstract].

Klepeis, et al., "Predicting Peptide Structures Using NMR Data and Deterministic Global Optimization", *Journal of Computational Chemistry*, vol. 20 (13), pp. 1354-1370 (1999).

Klepeis et al., "Integrated computational and experimental approach for lead optimization and design of compstatin variants with improved activity," *J. Am. Chem. Soc.*, vol. 125, pp. 8422-8423 (2003).

Kozlowski et al., "Development of pegylated interferons for the treatment of chronic hepatitis C", *BioDrugs*, vol. 15, pp. 419-429 (2001).

Mackerell et al., "All-Atom Empirical Potential for Molecular Modeling and Dynamics Studies of Proteins", *J. Phys. Chem.*, vol. B102, pp. 3586-3616 (1998).

Mallik, et al., "Conformational Interconversion in Compstatin Probed With Molecular Dynamics Simulations", *Proteins: Structure, Function, and Genetics*, vol. 52, pp. 130-141 (2003).

Mallik et al., "Development of a quasi-dynamic pharmacophore model for anti-complement peptide analogues", *J. Am. Chem. Soc.*, vol. 127, pp. 10967-10976 (2005).

Mallik et al., "Design and NMR Characterization of Active Analogs of Compstatin Containing Non-Natural Amino Acids", *J. Med. Chem.*, vol. 48, pp. 274-286 (2005).

Markiewski et al., "The Role of Complement in Inflammatory Diseases From Behind the Scenes into the Spotlight," *Am. J. Pathology*, vol. 171, pp. 715-727 (2007).

Martyna et al., "Constant pressure molecular dynamics algorithms", *J. Chem. Phys.*, vol. 101, pp. 4177-4189 (1994).

Morikis et al., "Solution structure of Compstatin, a potent complement inhibitor," *Protein Sci.*, vol. 7, pp. 619-627 (1998).

Morikis, et al., "Design, Structure, Function and Application of Compstatin", *Bioactive Peptides in Drug Discovery and Design: Medical Aspects*, J. Matsoukas and T. Mavromoustakos (Eds) IOS Press, pp. 235-246 (1999).

Morikis, et al., "Structural aspects and design of low-molecular-mass complement inhibitors", *Biochemical Society Transactions*, vol. 30 (6), pp. 1026-1036 (2002).

Morikis et al, "The structural basis of compstatin activity examined by structure-function-based design of peptide analogs and NMR," *J. Biol. Chem.*, vol. 277, pp. 14942-14953 (2002).

Mulakala et al., "A simple, yet highly accurate, QSAR model captures the complement inhibitory activity of compstatin," *Bioorg. Med. Chem.*, vol. 15, pp. 1638-1644 (2007).

Nguyen et al., "The pharmacokinetics of an albumin-binding Fab (AB.Fab) can be modulated as a function of affinity for albumin," *Protein Eng,. Des. & Sel.*, vol. 19, pp. 291-297 (2006).

Ngo, et al., "Computational Complexity, Protein Structure Prediction, and the Levinthal Paradox", *The Protein Folding Problem and Tertiary Structure Prediction*, pp. 492-495 (1994).

Nilsson et al., "Compstatin inhibits complement and cellular activation in whole blood in two models of extracorporeal circulation," *Blood*, vol. 92, pp. 1661-1667 (1998).

Phillips et al., "Scalable molecular dynamics with NAMD", *J. Comput. Chem.*, vol. 26, pp. 1781-1802 (2005).

Qu et al, "Novel Analogues of the Therapeutic Complement Inhibitor Compstatin with Significantly Improved Affinity and Potency," *Molecular Immunology*, vol. 48, No. 4, pp. 481-489 (2011).

Ricklin et al., "Compstatin: a Complement Inhibitor on its way to Clinical Application," *Adv. Exp. Med Biol.*, vol. 632, pp. 273-292 (2008).

Ricklin et al., "Complement-targeted therapeutics," *Nat. Biotechnol.*, vol. 25, pp. 1265-1275 (2007).

Robinson et al., "The design, structures and therapeutic potential of protein epitope mimetics," *Drug Disc. Today*, vol. 13, pp. 944-951 (2008).

Sahu et al., "Inhibition of Human Complement by a C3-binding Peptide Isolated from a Phage-Displayed Random Peptide Library," *J. Immunol*, vol. 157, pp. 884-891 (1996).

Sahu et al., "Binding Kinetics, Structure-Activity Relationship, and Biotransformation of the Complement Inhibitor Compstatin," *J. Immunol.*, vol. 165, pp. 2491-2499 (2000).

(56) References Cited

OTHER PUBLICATIONS

Sahu, et al., "Compstatin, a peptide inhibitor of complement, exhibits species-specific binding to complement component C3", *Molecular Immunology*, vol. 39, pp. 557-566 (2003).

Schasteen, et al., "Synthetic Peptide Inhibitors of Complement Serine Proteases—III. Significant Increase in Inhibitor Potency Provides Further Support for the Functional Equivalence Hypothesis", *Molecular Immunology*, vol. 28 (1/2), pp. 17-26 (1991).

Schmidt et al., "Inhibitor of complement, Compstatin, prevents polymer-mediated Mac-1 up-regulation of human neutrophils independent of biomaterial type tested," *J. Biomed. Mater. Res. A*, vol. 66, pp. 491-499 (2003).

Soulika et al., "Inhibition of heparin/protamine complex-induced complement activation by Compstatin in baboons," *Clin. Immunol.*, vol. 96, pp. 212-221 (2000).

Soulika, et al., "Studies of Structure-Activity Relations of Complement Inhibitor Compstatin", *The Journal of Immunology*, vol. 170, pp. 1881-1890 (2003).

Spruce, L., et al., "Chemical synthesis of small complement proteins and protein modules", *International Immunopharmacology*, vol. 2, pp. 1320-1321 (2002).

Tosic et al., "Preparation of monoclonal antibodies to C3b by immunization with C3b(i)-sepharose", *J. Immunol. Methods*, vol. 120(2), pp. 241-249, (1989).

Vagner et al., "Peptidomimetics, A synthetic tool of drug discovery," *Curr. Opin. Chem. Biol.*, vol. 12, pp. 292-296 (2008).

Veronese, F.M., "Peptide and protein PEGylation: a review of problems and solutions", *Biomaterials*, vol. 22, pp. 405-417 (2001).

Wang, Y., et al., "Amelioration of lupus-like autoimmune disease in NZB/WF1 mice after treatment with a blocking monoclonal antibody specific for complement component C5", *Proc. Natl. Acad. Sci. USA*, vol. 93, pp. 8563-8568 (1996).

Zacharias, et al., "Cation-$\pi$ interactions in ligand recognition and catalysis", *Trends in Pharmacological Sciences* 23 (6):281-287 (2002).

Zhao, B., et al., "A paradigm for drug discovery using a conformation from the crystal structure of a presentation scaffold", *Nat. Struct. Biol.*, vol. 2, pp. 1131-1137 (1995).

Non-Final Office Action in U.S. Appl. No. 11/605,182, mailed Jun. 30, 2009.

Final Office Action in U.S. Appl. No. 11/605,182, mailed Mar. 3, 2010.

Non-Final Office Action in U.S. Appl. No. 10/528,496, mailed Jun. 22, 2010.

Copending U.S. Appl. No. 61/385,711, Filing Receipt, dated Oct. 14, 2010,.

Notice of Allowance in U.S. Appl. No. 11/605,182, mailed Sep. 27, 2010.

International Search Report and Written Opinion in PCT/US2012/054180, issued Apr. 10, 2013.

International Search Report and Written Opinion in PCT/US2006/045539, mailed Jul. 24, 2007.

International Search Report and Written Opinion in PCT/US2010/033345, mailed Jul. 16, 2010.

Notice of Allowance in U.S. Appl. No. 10/528,496, mailed Mar. 22, 2011.

\* cited by examiner

SEQUENCE LISTING

<160> NUMBER OF SEQ ID NOS: 29

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)

```
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 2

Ile Cys Val Trp Gln Asp Trp Gly Ala His Arg Cys Thr
1               5                   10

<210> SEQ ID NO 3
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 3

Ile Cys Val Trp Gln Asp Trp Gly Ala His Arg Cys Ile
1               5                   10

<210> SEQ ID NO 4
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is missing or is Gly, Me-Gly, Tyr, Phe,
      Arg, Trp, Thr, Me-Tyr, Me-Phe, Me-Val, Me-Ile, Me-Ala, D-Tyr,
      D-Phe, D-Trp, D-Cha or D-Ala
<220> FEATURE:
<221> NAME/KEY: VARIANT
<222> LOCATION: (2)..(2)
<223> OTHER INFORMATION: Xaa is Ile, Me-Ile, Ac-Ile, Trp or Gly
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
```

```
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 4

Xaa Xaa Cys Val Trp Gln Asp Trp Gly Ala His Arg Cys Ile
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 5

Ile Cys Val Trp Gln Asp Trp Gly Ala His Arg Cys Ile
1               5                   10

<210> SEQ ID NO 6
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION
```

```
<400> SEQUENCE: 6

Gly Ile Cys Val Trp Gln Asp Trp Gly Ala His Arg Cys Ile
1               5                   10

<210> SEQ ID NO 7
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 7

Gly Ile Cys Val Trp Gln Asp Trp Gly Ala His Arg Cys Ile
1               5                   10

<210> SEQ ID NO 8
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 8

Tyr Ile Cys Val Trp Gln Asp Trp Gly Ala His Arg Cys Ile
1               5                   10

<210> SEQ ID NO 9
<211> LENGTH: 14
<212> TYPE: PRT
<213> ORGANISM: Artificial sequence
```

```
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 9

Phe Ile Cys Val Trp Gln Asp Trp Gly Ala His Arg Cys Ile
1               5                   10

<210> SEQ ID NO 10
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 10

Arg Ile Cys Val Trp Gln Asp Trp Gly Ala His Arg Cys Ile
1               5                   10

<210> SEQ ID NO 11
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
```

```
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 11

Trp Ile Cys Val Trp Gln Asp Trp Gly Ala His Arg Cys Ile
1               5                   10

<210> SEQ ID NO 12
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 12

Thr Ile Cys Val Trp Gln Asp Trp Gly Ala His Arg Cys Ile
1               5                   10

<210> SEQ ID NO 13
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 13

Tyr Ile Cys Val Trp Gln Asp Trp Gly Ala His Arg Cys Ile
1               5                   10
```

```
<210> SEQ ID NO 14
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 14

Phe Ile Cys Val Trp Gln Asp Trp Gly Ala His Arg Cys Ile
1               5                   10

<210> SEQ ID NO 15
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 15

Val Ile Cys Val Trp Gln Asp Trp Gly Ala His Arg Cys Ile
1               5                   10

<210> SEQ ID NO 16
<211> LENGTH: 14
<212> TYPE: PRT
<213> ORGANISM: Artificial sequence
<220> FEATURE:
```

```
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 16

Ile Ile Cys Val Trp Gln Asp Trp Gly Ala His Arg Cys Ile
1               5                   10

<210> SEQ ID NO 17
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: METHYLATION
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 17

Ala Ile Cys Val Trp Gln Asp Trp Gly Ala His Arg Cys Ile
1               5                   10

<210> SEQ ID NO 18
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
```

-continued

```
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 18

Xaa Ile Cys Val Trp Gln Asp Trp Gly Ala His Arg Cys Ile
1               5                   10

<210> SEQ ID NO 19
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Phe
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 19

Xaa Ile Cys Val Trp Gln Asp Trp Gly Ala His Arg Cys Ile
1               5                   10

<210> SEQ ID NO 20
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Trp
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
```

```
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 20

Xaa Ile Cys Val Trp Gln Asp Trp Gly Ala His Arg Cys Ile
1               5                   10

<210> SEQ ID NO 21
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Cha
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 21

Xaa Ile Cys Val Trp Gln Asp Trp Gly Ala His Arg Cys Ile
1               5                   10

<210> SEQ ID NO 22
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Ala
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
```

<221> NAME/KEY: MOD_RES
<222> LOCATION: (14)..(14)
<223> OTHER INFORMATION: AMIDATION

<400> SEQUENCE: 22

Xaa Ile Cys Val Trp Gln Asp Trp Gly Ala His Arg Cys Ile
1               5                   10

<210> SEQ ID NO 23
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (13)..(13)
<223> OTHER INFORMATION: METHYLATION
<220> FEATURE:
<221> NAME/KEY: MOD_RES
<222> LOCATION: (13)..(13)
<223> OTHER INFORMATION: AMIDATION

<400> SEQUENCE: 23

Trp Cys Val Trp Gln Asp Trp Gly Ala His Arg Cys Ile
1               5                   10

<210> SEQ ID NO 24
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 24

Tyr Gly Cys Val Trp Gln Asp Trp Gly Ala His Arg Cys Ile
1               5                   10

<210> SEQ ID NO 25

```
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (12)..(12)
<223> OTHER INFORMATION: Xaa is Orn
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 25

Xaa Ile Cys Val Trp Gln Asp Trp Gly Ala His Xaa Cys Ile
1               5                   10

<210> SEQ ID NO 26
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 26

Xaa Ile Cys Val Trp Gln Asn Trp Gly Ala His Arg Cys Ile
1               5                   10

<210> SEQ ID NO 27
<211> LENGTH: 14
<212> TYPE: PRT
<213> ORGANISM: Artificial sequence
```

```
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is D-Tyr
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MOD_RES
<222> LOCATION: (12)..(12)
<223> OTHER INFORMATION: Xaa is Orn
<220> FEATURE:
<221> NAME/KEY: MOD_RES
<222> LOCATION: (14)..(14)
<223> OTHER INFORMATION: METHYLATION
<220> FEATURE:
<221> NAME/KEY: MOD_RES
<222> LOCATION: (14)..(14)
<223> OTHER INFORMATION: AMIDATION

<400> SEQUENCE: 27

Xaa Ile Cys Val Trp Gln Asn Trp Gly Ala His Xaa Cys Ile
1               5                  10

<210> SEQ ID NO 28
<211> LENGTH: 15
<212> TYPE: PRT
<213> ORGANISM: Artificial sequence
<220> FEATURE:
<223> OTHER INFORMATION: synthetic sequence

<400> SEQUENCE: 28

Leu Arg Phe Leu Asn Pro Phe Ser Leu Asp Gly Ser Gly Phe Trp
1               5                  10                  15

<210> SEQ ID NO 29
<211> LENGTH: 14
<212> TYPE: PRT
<213> ORGANISM: Artificial sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is missing or is Tyr, D-Tyr or N-methyl Gly
<220> FEATURE:
<221> NAME/KEY: VARIANT
<222> LOCATION: (2)..(2)
<223> OTHER INFORMATION: Xaa is Ile, Gly or Ac-Trp
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (7)..(7)
<223> OTHER INFORMATION: Xaa is Asp or Asn
<220> FEATURE:
<221> NAME/KEY: VARIANT
<222> LOCATION: (8)..(8)
<223> OTHER INFORMATION: Xaa is Trp or an analog of Trp
<220> FEATURE:
```

```
<221> NAME/KEY: MOD_RES
<222> LOCATION: (9)..(9)
<223> OTHER INFORMATION: METHYLATION (optional)
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (12)..(12)
<223> OTHER INFORMATION: Xaa is Arg or Orn
<220> FEATURE:
<221> NAME/KEY: VARIANT
<222> LOCATION: (14)..(14)
<223> OTHER INFORMATION: Xaa is Thr, Ile, Leu, Nle, N-methyl Thr or
      N-methyl Ile
<220> FEATURE:
<221> NAME/KEY: MOD_RES
<222> LOCATION: (14)..(14)
<223> OTHER INFORMATION: AMIDATION (optional)

<400> SEQUENCE: 29

Xaa Xaa Cys Val Xaa Gln Xaa Xaa Gly Xaa His Xaa Cys Xaa
1               5                   10
```

COMPSTATIN ANALOGS WITH IMPROVED PHARMACOKINETIC PROPERTIES

This is a U.S. national filing, pursuant to 35 U.S.C. §371, of International Application No. PCT/US2012/054180, filed Sep. 7, 2012, which claims benefit of U.S. Provisional Application No. 61/531,919, filed Sep. 7, 2011, and U.S. Provisional Application No. 61/651,204, filed May 24, 2012.

GOVERNMENT SUPPORT

This invention was made with government support under GM62134, AI30040, AI068730, GM097747 and EY020633, awarded by the National Institutes of Health. The government has certain rights in the invention.

FIELD OF THE INVENTION

This invention relates to activation of the complement cascade in the body. In particular, this invention provides peptides and peptidomimetics that bind the C3 protein with nanomolar affinity and inhibit complement activation, exhibit robust aqueous solubility, plasma stability and in vivo retention and are bioavailable by multiple routes of administration.

BACKGROUND OF THE INVENTION

Various publications, including patents, published applications, technical articles and scholarly articles are cited throughout the specification. Each of these cited publications is incorporated by reference herein, in its entirety.

The human complement system is a powerful player in the defense against pathogenic organisms and the mediation of immune responses. Complement can be activated through three different pathways: the classical, lectin, and alternative pathways. The major activation event that is shared by all three pathways is the proteolytic cleavage of the central protein of the complement system, C3, into its activation products C3a and C3b by C3 convertases. Generation of these fragments leads to the opsonization of pathogenic cells by C3b and iC3b, a process that renders them susceptible to phagocytosis or clearance, and to the activation of immune cells through an interaction with complement receptors (Markiewski & Lambris, 2007, *Am J Pathol* 171: 715-727). Deposition of C3b on target cells also induces the formation of new convertase complexes and thereby initiates a self-amplification loop.

An ensemble of plasma and cell surface-bound proteins carefully regulates complement activation to prevent host cells from self-attack by the complement cascade. However, excessive activation or inappropriate regulation of complement can lead to a number of pathologic conditions, ranging from autoimmune to inflammatory diseases (Holers, 2003, *Clin Immunol* 107: 140-51; Markiewski & Lambris, 2007, supra; Ricklin & Lambris, 2007, *Nat Biotechnol* 25: 1265-75; Sahu et al., 2000, *J Immunol* 165: 2491-9). The development of therapeutic complement inhibitors is therefore highly desirable. In this context, C3 and C3b have emerged as promising targets because their central role in the cascade allows for the simultaneous inhibition of the initiation, amplification, and downstream activation of complement (Ricklin & Lambris, 2007, supra).

Compstatin was the first non-host-derived complement inhibitor that was shown to be capable of blocking all three activation pathways (Sahu et al., 1996, *J Immunol* 157: 884-91; U.S. Pat. No. 6,319,897). This cyclic tridecapeptide binds to both C3 and C3b and prevents the cleavage of native C3 by the C3 convertases. Its high inhibitory efficacy was confirmed by a series of studies using experimental models that pointed to its potential as a therapeutic agent (Fiane et al., 1999a, *Xenotransplantation* 6: 52-65; Fiane et al., 1999b, *Transplant Proc* 31:934-935; Nilsson et al., 1998 *Blood* 92: 1661-1667; Ricklin & Lambris, 2008, *Adv Exp Med Biol* 632: 273-292; Schmidt et al., 2003, *J Biomed Mater Res A* 66: 491-499; Soulika et al., 2000, *Clin Immunol* 96: 212-221). Progressive optimization of compstatin has yielded analogs with improved activity (Ricklin & Lambris, 2008, supra; WO2004/026328; WO2007/062249). One of these analogs is currently being tested in clinical trials for the treatment of age-related macular degeneration (AMD), the leading cause of blindness in elderly patients in industrialized nations (Coleman et al., 2008, *Lancet* 372: 1835-1845; Ricklin & Lambris, 2008, supra). In view of its therapeutic potential in AMD and other diseases, further optimization of compstatin to achieve an even greater efficacy is of considerable importance.

Earlier structure-activity studies have identified the cyclic nature of the compstatin peptide and the presence of both β-turn and hydrophobic cluster as key features of the molecule (Morikis et al., 1998, *Protein Sci* 7: 619-627; WO99/13899; Morikis et al., 2002, *J Biol Chem* 277:14942-14953; Ricklin & Lambris, 2008, supra). Hydrophobic residues at positions 4 and 7 were found to be of particular importance, and their modification with unnatural amino acids generated an analog with 264-fold improved activity over the original compstatin peptide (Katragadda et al., 2006, *J Med Chem* 49: 4616-4622; WO2007/062249).

While previous optimization steps have been based on combinatorial screening studies, solution structures, and computational models (Chiu et al., 2008, *Chem Biol Drug Des* 72: 249-256; Mulakala et al., 2007, *Bioorg Med Chem* 15: 1638-1644; Ricklin & Lambris, 2008, supra), the publication of a co-crystal structure of compstatin complexed with the complement fragment C3c (Janssen et al., 2007, *J Biol Chem* 282: 29241-29247; WO2008/153963) represents an important milestone for initiating rational optimization. The crystal structure revealed a shallow binding site at the interface of macroglobulin (MG) domains 4 and 5 of C3c and showed that 9 of the 13 amino acids were directly involved in the binding, either through hydrogen bonds or hydrophobic effects. As compared to the structure of the compstatin peptide in solution (Morikis et al., 1998, supra), the bound form of compstatin experienced a conformational change, with a shift in the location of the β-turn from residues 5-8 to 8-11 (Janssen et al., 2007, supra; WO2008/153963).

The present inventors recently developed a series of compstatin analogs with improved potency based on N-methylation of the peptide backbone, particularly at position 8 of the peptide, and substitutions at the flanking position 13 (Qu et al., 2011, *Molec Immunol* 48: 481-489, WO2010/127336). Those modifications were reported to produce a compstatin analog with improved binding affinity over the most active analogs reported to date.

Compstatin and its analogs have significant potential for clinical applications. Recent examples include the reduction of filter-induced adverse effects during hemodialysis and organ preservation in sepsis. Importantly, the intravitreal use of compstatin analogs has shown promising results in the treatment of age-related macular degeneration (AMD), both in non-human primate (NHP) studies and in phase I clinical trials. The low molecular weight of compstatin and its analogs, their high specificity and efficacy, and their ability to simultaneously inhibit all complement activation and amplification pathways contribute to a beneficial drug profile. Extended clinical applications (e.g., systemic administration by a variety of routes), however, place additional demands on the molecular properties of compstatin derivatives. For instance, disfavored pharmacokinetic profiles due to rapid elimination from plasma still impose a major limitation for the clinical use of peptidic drugs. Additionally, though oral delivery is the most convenient and popular route of drug administration, most peptide drugs display little or no oral activity. This is believed to be due mainly to degradation in the gastrointestinal tract by enzymes and extreme conditions, as well as poor permeability of the intestinal mucosa. Consequently, most protein-based therapeutics are administered by frequent injections through the parenteral routes such as by intravenous, intramuscular and subcutaneous injection. These forms of administration are costly and can require a medical professional, all of which can result in poor patient acceptance and compliance. In view of the foregoing, it is clear that the development of modified compstatin peptides or mimetics with greater activity, in vivo stability, plasma residence time and bioavailability would constitute a significant advance in the art.

SUMMARY OF THE INVENTION

The present invention provides analogs of the complement-inhibiting peptide, compstatin, which maintain improved complement-inhibiting activity as compared to compstatin, and which also possess improved solubility and stability and pharmacokinetic properties, including bioavailability via multiple routes of administration.

One aspect of the invention features a compound comprising a modified compstatin peptide (ICVVQD-WGHHRCT (cyclic C2-C12; SEQ ID NO:1) or analog thereof, wherein the modification comprises an added or substituted N-terminal component that improves (1) the peptide's C3, C3b or C3c binding affinity, (2) the peptide's solubility in aqueous liquids, and/or (3) the peptide's plasma stability and/or plasma residence time, as compared with an unmodified compstatin peptide under equivalent conditions.

Components that can be added to the N-terminus of the peptide comprise amino acid residues other than L-Gly, or peptidic or non-peptidic analogs of such amino acids. In certain embodiments, the added component is a D-amino acid, and/or the component can include at least one aromatic ring. In one embodiment, the added component is D-Tyr. In other embodiments, the added component comprises an N-methylated amino acid. In one embodiment, the N-methylated amino acid is N-methylated L-Gly, also referred to herein as Sar. Thus, in various embodiments, the added component is D-Tyr, D-Phe, Tyr(Me), D-Trp, Tyr, D-Cha, Cha, Phe, Sat, Arg, mPhe, mVal, Trp, mIle, D-Ala, mAla, Thr or Tyr.

In other embodiments, the modified compstatin peptide comprises a substituted N-terminal component wherein Ile at position 1 is replaced with Ac-Trp or a dipeptide Tyr-Gly.

The compound can also include other modifications. For instance, His at position 9 (based on numbering of compstatin) can be replaced with Ala. Additionally, Val at position 4 can be replaced with Trp or an analog of Trp. Particular analogs of Trp at position 4 include 1-methyl Trp or 1-formyl Trp. The Trp at position 7 can also be replaced with an analog of Trp, including but not limited to a halogenated Trp. Other modifications include modification of Gly at position 8 to constrain the backbone conformation at that location. In particular, the backbone can be constrained by replacing the Gly at position 8 (Gly8) with $N^\alpha$-methyl Gly (Sar). Other modifications include replacing the Thr at position 13 with Ile, Leu, Nle, N-methyl Thr or N-methyl Ile. Still other modifications include replacing the disulfide bond between C2 and C12 with a thioether bond to form a cystathionine or a lanthionine Yet another modification includes replacing the Arg at position 11 with Orn, and/or replacing the Asp at position 6 with Asn.

In particular embodiments, the compstatin analog comprises a peptide having a sequence of SEQ ID NO:29, which is: Xaa1-Xaa2-Cys-Val-Xaa3 Gln-Xaa4 Xaa5-Gly-Xaa6-His-Xaa7-Cys-Xaa8, in which Gly between Xaa5 and Xaa6 (position 8 of compstatin) optionally is modified to constrain the backbone conformation, and wherein: Xaa1 is absent or is Tyr, D-Tyr or Sar; Xaa2 is Ile, Gly or Ac-Tip; Xaa3 is Trp or an analog of Trp, wherein the analog of Trp has increased hydrophobic character as compared with Trp; Xaa4 is Asp or Asn; Xaa5 is Trp or an analog of Tip comprising a chemical modification to its indole ring wherein the chemical modification increases the hydrogen bond potential of the indole ring; Xaa6 is His, Ala, Phe or Trp; Xaa7 is Arg or Orn; and Xaa8 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —$NH_2$, and wherein the peptide is cyclic via a Cys-Cys or thioether bond.

Particular embodiments of the analog include the following features: the Gly at position 8 is N-methylated; Xaa1 is D-Tyr or Sar; Xaa2 is Ile; Xaa3 is Trp, 1-methyl-Trp or 1-formyl-Trp; Xaa5 is Trp; Xaa6 is Ala; and Xaa8 is Thr, Ile, Leu, Nle, N-methyl Thr or N-methyl Ile with optional replacement of the carboxy terminal —OH with —$NH_2$. More specifically, Xaa8 can be Ile, N-methyl Thr or N-methyl Ile with optional replacement of the carboxy terminal —OH with —$NH_2$. Exemplary analogs include SEQ ID NO:7 and SEQ ID NO:18. Another aspect of the invention features a compound that inhibits complement activation, comprising a non-peptide or partial peptide mimetic of SEQ ID NO:7 or SEQ ID NO:18, wherein the compound binds C3 and inhibits complement activation with at least 500-fold greater activity than does a peptide comprising SEQ ID NO:1 under equivalent assay conditions.

Another aspect of the invention features a compound as described above, which includes an additional component that extends the in vivo retention (i.e., residence time) of the compound. In one embodiment, the additional component is polyethylene glycol (PEG). In other embodiments, the additional component is an albumin binding small molecule or an albumin binding peptide. In particular embodiments, the albumin binding small molecule or albumin binding peptide is attached to the peptide at the N- or C-terminus. The attachment can be direct or through a linker or spacer.

Another aspect of the invention features a pharmaceutical composition comprising any of the above-described compounds and a pharmaceutically acceptable carrier. In one embodiment, the pharmaceutical composition is formulated for oral administration. In another embodiment, it is formulated for topical administration. In another embodiment, it is formulated for pulmonary administration. In another embodiment, the pharmaceutical composition is formulated for subcutaneous or intramuscular injection. In another embodiment, it is formulated for intravenous injection or infusion.

Another aspect of the invention provides for the use of any of the above-described compounds for inhibition of complement activation in vivo, ex vivo, in situ or in vitro, as well as for use in the manufacture of a medicament for the inhibition of complement activation.

Various features and advantages of the present invention will be understood by reference to the detailed description, drawings and examples that follow.

DETAILED DESCRIPTION OF ILLUSTRATIVE EMBODIMENTS

Definitions

Figure 1:
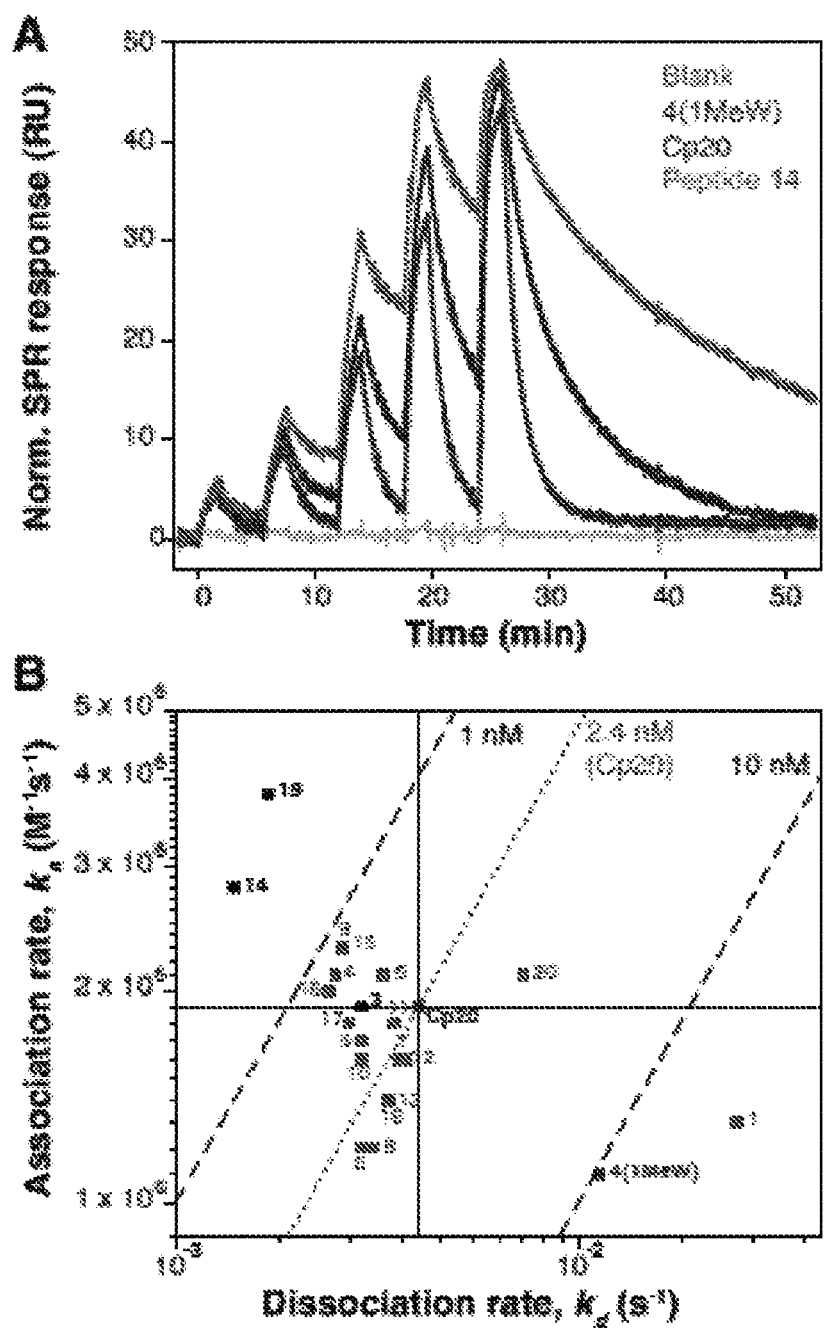
FIG. 1. Interaction of compstatin analogs with C3b. (A) Kinetic profiles of compstatin lead compounds 4 (1 MeW) (lowest, narrowest set of peaks), Cp20 (SEQ ID NO:3) (intermediate set of peaks), and peptide 14 (Cp40 (SEQ ID NO:18)) (highest, broadest set of peaks) as determined by single cycle kinetic analysis using surface plasmon resonance. (B) Rate plot of peptides 1-20 as well as reference compounds 4 (1 MeW) and Cp20 (SEQ ID NO:3) with isoaffinity lines shown as dashed lines. Benchmark lines for the rate constant and affinity of Cp20 (SEQ ID NO:3) are shown.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations may be used herein: Ac, acetyl group; DCM, dichloromethane; DIC, 1,3-diisopropylcarbodiimide; DIPEA, N,N-diisopropylethylamine; DPBS, Dulbecco's Phosphate Buffered Saline; ELISA, enzyme-linked immunosorbent assay; ESI, electrospray ionization; Fmoc, 9-fluorenylmethoxycarbonyl; HOAt, 1-hydroxy-7-aza-benzotriazole; ITC, Isothermal titration calorimetry; MALDI, matrix-assisted laser desorption ionization; MBHA, 4-methylbenzhydrylamine; NMP, N-methylpyrrolidinone; Sar, N-methyl glycine; SPR, surface plasmon resonance; TIPS, triisopropylsilane; Trt, trityl; WFI, water for injection.

The term "about" as used herein when referring to a measurable value such as an amount, a temporal duration, and the like, is meant to encompass variations of ±20% or ±10%, in some embodiments ±5%, in some embodiments ±1%, and in some embodiments ±0.1% from the specified value, as such variations are appropriate to make and used the disclosed compounds and compositions.

The term "compstatin" as used herein refers to a peptide comprising SEQ ID NO:1, ICVVQDWGHHRCT (cyclic C2-C12 by way of a disulfide bond). The term "compstatin analog" refers to a modified compstatin comprising substitutions of natural and/or unnatural amino acids, or amino acid analogs, as well as modifications within or between various amino acids, as described in greater detail herein, and as known in the art. When referring to the location of particular amino acids or analogs within compstatin or compstatin analogs, those locations are sometimes referred to as "positions" within the peptide, with the positions numbered from 1 (Ile in compstatin) to 13 (Thr in compstatin). For example, the Gly residue occupies "position 8."

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to an optionally substituted saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl. The term "lower alkyl" refers to an optionally substituted saturated straight, branched, or cyclic hydrocarbon having from about 1 to about 5 carbon atoms (and all combinations and subcombinations of ranges and specific numbers of carbon atoms therein). Lower alkyl groups include, but are not limited to, methyl, ethyl, n-propyl, isopropyl, n-butyl, isobutyl, t-butyl, n-pentyl, cyclopentyl, isopentyl and neopentyl.

As used herein, "halo" refers to F, Cl, Br or I.

As used herein, "alkanoyl", which may be used interchangeably with "acyl", refers to an optionally substituted straight or branched aliphatic acylic residue having from about 1 to about 10 carbon atoms (and all combinations and subcombinations of ranges and specific numbers of carbon atoms therein), with from about 1 to about 7 carbon atoms being preferred Alkanoyl groups include, but are not limited to, formyl, acetyl, propionyl, butyryl, isobutyryl, pentanoyl, isopentanoyl, 2-methyl-butyryl, 2,2-dimethylpropionyl, hexanoyl, heptanoyl, octanoyl, and the like. The term "lower alkanoyl" refers to an optionally substituted straight or branched aliphatic acylic residue having from about 1 to about 5 carbon atoms (and all combinations and subcombinations of ranges and specific numbers of carbon atoms therein. Lower alkanoyl groups include, but are not limited to, formyl, acetyl, n-propionyl, iso-propionyl, butyryl, isobutyryl, pentanoyl, iso-pentanoyl, and the like.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl as defined above, bearing an aryl substituent and having from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy, among others.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen at selected locations on a molecule. Exemplary substituents include, for example, halo, alkyl, cycloalkyl, aralkyl, aryl, sulfhydryl, hydroxyl (—OH), alkoxyl, cyano (—CN), carboxyl (—COOH), acyl (alkanoyl: —C(=O)R); —C(=O)O-alkyl, aminocarbonyl (—C(=O)NH$_2$), —N— substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term "D-amino acid" refers to dextrorotatory alpha-amino acids. Unless specified otherwise, all amino acids referred to herein are L-amino acids.

"Hydrophobic" or "nonpolar" are used synonymously herein, and refer to any inter- or intra-molecular interaction not characterized by a dipole.

"PEGylation" refers to the reaction in which at least one polyethylene glycol (PEG) moiety, regardless of size, is chemically attached to a protein or peptide to form a PEG-peptide conjugate. "PEGylated means that at least one PEG moiety, regardless of size, is chemically attached to a peptide or protein. The term PEG is generally accompanied by a numeric suffix that indicates the approximate average molecular weight of the PEG polymers; for example, PEG-8,000 refers to polyethylene glycol having an average molecular weight of about 8,000 Daltons (or g/mol).

As used herein, "pharmaceutically acceptable salts" refers to derivatives of the disclosed compounds wherein the parent compound is modified by making acid or base salts thereof. Examples of pharmaceutically-acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

Description

The present invention springs in part from the inventors' development of compstatin analogs displaying improvements in both inhibitory potency and pharmacokinetic parameters. Selective modification of the compstatin N-terminus with non-proteinogenic amino acids and/or other molecular entities resulted in certain analogs with subnanomolar binding affinity (K$_D$=0.5 nM) and other similarly potent derivatives with improved solubility in clinically relevant solvents. Pharmacokinetic evaluation in non-human primates revealed plasma half-life values exceeding expectations for peptidic drugs. Bioavailability evaluation in two non-human primate models demonstrated subcutaneous, intramuscular and oral bioavailability of certain analogs.

One modification in accordance with the present invention comprises adding a component to the N-terminus of compstatin (Ile-[Cys-Val-Val-Gln-Asp-Trp-Gly-His-His-Arg-Cys]-Thr; SEQ ID NO:1) that improves solubility and plasma stability of the peptide, while maintaining or improving C3 binding affinity and complement inhibitory activity. In particular embodiments, the added component is an amino acid residue, particularly a residue that resists proteolytic cleavage, such as an N-methylated amino acid (e.g., N-methyl Gly (Sar), or a D-amino acid (e.g., D-Tyr)). Also, as discussed in greater detail below, the D configuration of the N-terminal residue may better configure the free amino group for polar interaction with C3. Additionally, amino acids or analogs comprising a hydrophobic side chain (e.g., including an aromatic ring) at the N-terminus facilitates binding to C3, likely via interaction with a hydrophobic pocket at the compstatin-C3 binding site.

Reference is made to the exemplary analogs set forth below, which show significantly improved activity over compstatin and even the potent analog, Ac-Ile-[Cys-Val-Trp (Me)-Gln-Asp-Trp-Gly-Ala-His-Arg-Cys]-Thr-NH$_2$ (SEQ ID NO:2) (Katragadda et al., 2006, supra, WO 2007/062249; sometimes referred to herein as "4 (1 MeW)"), as well as several other favorable characteristics discussed in detail below.

```
"Compstatin 30" (Cp30):
Sar-Ile-[Cys-Val-Trp(Me)-Gln-Asp-Trp-Sar-Ala-His-

Arg-Cys]-mIle-NH2
(SEQ ID NO: 7; also referred to in the Examples
as "peptide 3")

"Compstatin 40" (Cp40):
dTyr-Ile-[Cys-Val-Trp(Me)-Gln-Asp-Trp-Sar-Ala-His-

Arg-Cys]-mIle-NH2
(SEQ ID NO: 18; also referred to in the Examples
as "peptide 14")
```

Without intending to be bound or limited by theory, it is believed that the improved C3 binding affinity of the analogs described herein is due at least in part to higher affinity interactions mediated by the N-terminus. For instance, SPR and ELISA data indicate that D-amino acids, or amino acids with hydrophobic side chains improved C3 binding, while the combination of features, i.e., D-amino acids with aromatic side chains e.g., D-Tyr), were most advantageous. In general, D-amino acids with aromatic side chains were shown to be favored over amino acids with shorter side chains in either D or L configuration. Furthermore, docking studies indicate that the improved affinity stems from additional polar and non-polar interactions involving the positioning of the free amino group, and the nature and positioning of the side chain on the N-terminal residue. For instance, the affinity gain of Cp40 (SEQ ID NO:18) was determined to be due at least in part from a combination of interactions with C3 at the N-terminus of the analog; (1) the D configuration of the N-terminal Tyr better presented the free amino group for polar interaction with C3, a feature that also explains the advantage of the D configuration overall; and (2) the bulky hydrophobic side chain was able to fit into a hydrophobic pocket on C3c and also presented a hydroxyl group for hydrogen bonding with C3c. In addition, docking studies predicted an analog comprising Ac-Trp at the N-terminus (Example 2) to bind C3 with high affinity. SPR analysis of peptide 1 indeed showed high binding affinity, comparable to that of Cp40 (SEQ ID NO:18) (peptide 14). It was determined that both peptides utilize the hydrophobic binding pocket on C3, C3b or C3c, proximal to the N-terminus of compstatin.

N-methylation can affect a peptide in several ways. First, a potential hydrogen bond donor is replaced with a methyl group, which cannot form a hydrogen bond. Second, the N-methyl group is weakly electron-donating which means it can slightly increase the basicity of the neighboring carbonyl group. Third, the size of the N-methyl group could cause steric constraint, depending on the nature of the neighboring residues. Finally, the N-methylation can change the trans/cis population of the amide bond, thus changing local peptide conformation in a manner similar to a proline. In the case of Cp30 (SEQ ID NO:7), SPR data indicate slightly faster associate rate and slower dissociate rate than Cp20 (SEQ ID NO:3), which suggests that Cp30 (SEQ ID NO:7) has more favorable free solution conformation for binding to C3/C3b/C3c and the binding is stronger. Considering the absence of an Ac group and the presence of a methyl group in the N-terminal position, it is reasonable to surmise that the modification allowed the N-terminus to take part in stronger polar interaction with residues S388/S437/D349 of C3c. This was made possible by positioning the free N-terminus to a favorable position via N-methylation in a way that enhances polar interactions with the binding site on C3/C3c.

In addition to improved C3 binding affinity, the analogs of the present invention possess improved solubility characteristics as compared with previously available analogs, such as Cp20 (SEQ ID NO:3). For systemic pharmacological administration, analogs with high solubility in both water for injection (WFI) and phosphate-buffered saline (PBS) are desirable to minimize the required injection volume. By comparison, analogs with a high solubility in WFI and lower solubility in PBS could produce a more long-lasting gel, precipitate or suspension for topical application or local injection, such as intraocular injection, e.g., for treatment of AMD. It was determined that Cp30 (SEQ ID NO:7) was soluble in both WFI and PBS, while Cp40 (SEQ ID NO:18) was less soluble in PBS than in WFI.

The peptide analogs of the invention further display favorable plasma stability characteristics, believed to be due at least in part to the presence of one or more N-terminal components that resist protease attack, e.g., a D-amino acid residue or an N-methyl group, or albumin-binding molecules. In addition, the analogs bind specifically and robustly to C3, C3b and C3c in plasma. Importantly, the stability afforded by the N-terminal and/or other modifications described herein contribute to improved bioavailability from oral, subcutaneous or intramuscular administration, as demonstrated in mouse and two non-human primate model systems, as well as improved (i.e., slower) plasma elimination half-live values of the analogs in vivo, as demonstrated in primate model systems.

The above-described N-terminal modifications can be combined with other modifications of compstatin previously shown to improve activity, thereby producing peptides with significantly improved complement inhibiting activity. For example, acetylation of the N-terminus typically increases the complement-inhibiting activity of compstatin and its analogs. Accordingly, addition of an acyl group at the amino terminus of the peptide, including but not limited to N-acetylation, is one embodiment of the invention, though may not be needed if the N-terminus of the peptide is already stable, or if solubility becomes an issue.

As another example, it is known that substitution of Ala for His at position 9 improves activity of compstatin and is a preferred modification of the peptides of the present invention as well. It has also been determined that substitution of Tyr for Val at position 4 can result in a modest improvement in activity (Klepeis et al., 2003, *J Am Chem Soc* 125: 8422-8423).

It was disclosed in WO2004/026328 and WO2007/0622249 that Trp and certain Trp analogs at position 4, as well as certain Trp analogs at position 7, especially combined with Ala at position 9, yields many-fold greater activity than that of compstatin. These modifications are used to advantage in the present invention as well.

In particular, peptides comprising 5-fluoro-tryptophan or either 5-methoxy-, 5-methyl- or 1-methyl-tryptophan, or 1-formyl-tryptophan at position 4 have been shown to possess 31-264-fold greater activity than compstatin. Particularly preferred are 1-methyl and 1-formyl tryptophan. It is believed that an indole 'N'-mediated hydrogen bond is not necessary at position 4 for the binding and activity of compstatin. The absence of this hydrogen bond or reduction of the polar character by replacing hydrogen with lower alkyl, alkanoyl or indole nitrogen at position 4 enhances the binding and activity of compstatin. Without intending to be limited to any particular theory or mechanism of action, it is believed that a hydrophobic interaction or effect at position 4 strengthens the interaction of compstatin with C3. Accordingly, modifications of Trp at position 4 (e.g., altering the structure of the side chain according to methods well known in the art), or substitutions at position 4 or position 7 of Trp analogs that maintain or enhance the aforementioned hydrophobic interaction are contemplated in the present invention as an advantageous modification in combination with the modifications at positions 8 and 13 as described above. Such analogs are well known in the art and include, but are not limited to the analogs exemplified herein, as well as unsubstituted or alternatively substituted derivatives thereof. Examples of suitable analogs may be found by reference to the following publications, and many others: Beene, et al., 2002, *Biochemistry* 41: 10262-10269 (describing, inter alia, singly- and multiply-halogenated Trp analogs); Babitzky & Yanofsky, 1995, *J. Biol. Chem.* 270: 12452-12456 (describing, inter alia, methylated and halogenated Trp and other Trp and indole analogs); and U.S. Pat. Nos. 6,214,790, 6,169,057, 5,776,970, 4,870,097, 4,576,750 and 4,299,838. Trp analogs may be introduced into the compstatin peptide by in vitro or in vivo expression, or by peptide synthesis, as known in the art.

In certain embodiments, Trp at position 4 of compstatin is replaced with an analog comprising a 1-alkyl substituent, more particularly a lower alkyl (e.g., $C_1$-$C_5$) substituent as defined above. These include, but are not limited to, N($\alpha$) methyl tryptophan and 5-methyltryptophan. In other embodiments, Trp at position 4 of compstatin is replaced with an analog comprising a 1-alkanoyl substituent, more particularly a lower alkanoyl (e.g., $C_1$-$C_5$) substituent as defined above, e.g., N($\alpha$) formyl tryptophan, 1-acetyl-L-tryptophan and L-$\beta$-homotryptophan.

It was disclosed in WO2007/0622249 that incorporation of 5-fluoro-tryptophan at position 7 in compstatin increased the enthalpy of the interaction between the resulting compstatin analog and C3, relative to compstatin, whereas incorporation of 5-fluoro-tryptophan at position 4 in decreased the enthalpy of this interaction. Accordingly, modifications of Trp at position 7, as described in WO2007/0622249, are contemplated as useful modifications in combination with the N-terminal modifications described above.

Other modifications are described in WO2010/127336. One modification disclosed in that document comprises constraint of the peptide backbone at position 8 of the peptide. In a particular embodiment, the backbone is constrained by replacing glycine at position 8 ($Gly^8$) with N-methyl glycine. Another modification disclosed in that document comprises replacing Thr at position 13 with Ile, Leu, Nle (norleucine), N-methyl Thr or N-methyl Ile.

Still other modifications are described in co-pending Application No. 61/385,711. One such modification comprises replacement of the C2-C12 disulfide bond with addition of a $CH_2$ to form a homocysteine at C2 or C12, and introduction of a thioether bond, to form a cystathionine, such as a gamma-cystathionine or a delta-cystathionine Another modification comprises replacement of the C2-C12 disulfide bond with a thioether bond without the addition of a $CH_2$, thereby forming a lanthionine. The analogs comprising the thioether bond demonstrate activity that is substantially the same as that of certain of the disulfide bond analogs and also possess equivalent or improved stability characteristics.

Yet other internal modifications are described in the present application. For instance, substituting ornithine for arginine at position 11, and/or substituting asparagine for aspartic acid at position 6 of certain compstatin analogs (e.g. Cp20, SEQ ID NO:3, Cp40, SEQ ID NO:18), results in analogs with binding and complement inhibitory activity similar to the parent compounds. In addition, one or both of those substitutions is expected to render the analogs less susceptible to metabolism by certain physiological enzymes found in the intestinal tract, liver or plasma.

The modified compstatin peptides of the present invention may be prepared by various synthetic methods of peptide synthesis via condensation of one or more amino acid residues, in accordance with conventional peptide synthesis methods. For example, peptides are synthesized according to standard solid-phase methodologies. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly known protecting groups. An example of a suitable peptide synthetic method is set forth in Example L Modification utilizing alternative protecting groups for peptides and peptide derivatives will be apparent to those of skill in the art.

Alternatively, certain peptides of the invention may be produced by expression in a suitable prokaryotic or eukaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptides can also be produced by expression of a nucleic acid molecule in vitro or in vivo. A DNA construct encoding a concatemer of the peptides, the upper limit of the concatemer being dependent on the expression system utilized, may be introduced into an in vivo expression system. After the concatemer is produced, cleavage between the C-terminal Asn and the following N-terminal G is accomplished by exposure of the polypeptide to hydrazine.

The peptides produced by gene expression in a recombinant procaryotic or eucaryotic system may be purified according to methods known in the art. A combination of gene expression and synthetic methods may also be utilized to produce compstatin analogs. For example, an analog can be produced by gene expression and thereafter subjected to one or more post-translational synthetic processes, e.g., to modify the N- or C-terminus or to cyclize the molecule.

Advantageously, peptides that incorporate unnatural amino acids, e.g., methylated amino acids, may be produced by in vivo expression in a suitable prokaryotic or eukaryotic system. For example, methods such as those described by Katragadda & Lambris (2006, *Protein Expression and Purification* 47: 289-295) to introduce unnatural Trp analogs into compstatin via expression in *E. coli* auxotrophs may be utilized to introduce N-methylated or other unnatural amino acids at selected positions of compstatin.

The structure of compstatin is known in the art, and the structures of the foregoing analogs are determined by similar means. Once a particular desired conformation of a short peptide has been ascertained, methods for designing a peptide or peptidomimetic to fit that conformation are well known in the art. Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Vagner et al., 2008, *Curt. Opin. Chem. Biol.* 12: 292-296; Robinson et al., 2008, *Drug Disc. Today* 13: 944-951) Assuming rotational constraints similar to those of amino acid residues within a peptide, analogs comprising non-amino acid moieties may be analyzed, and their conformational motifs verified, by any variety of computational techniques that are well known in the art.

The modified compstatin peptides of the present invention can be modified by the addition of polyethylene glycol (PEG) components to the peptide. As is well known in the art, PEGylation can increase the half-life of therapeutic peptides and proteins in vivo. In one embodiment, the PEG has an average molecular weight of about 1,000 to about 50,000. In another embodiment, the PEG has an average molecular weight of about 1,000 to about 20,000. In another embodiment, the PEG has an average molecular weight of about 1,000 to about 10,000. In an exemplary embodiment, the PEG has an average molecular weight of about 5,000. The polyethylene glycol may be a branched or straight chain, and preferably is a straight chain.

The compstatin analogs of the present invention can be covalently bonded to PEG via a linking group. Such methods are well known in the art. (Reviewed in Kozlowski A. et al. 2001, *BioDrugs* 15: 419-29; see also, Harris J M and Zalipsky S, eds. Polyethylene glycol), Chemistry and Biological Applications, ACS Symposium Series 680 (1997)). Non-limiting examples of acceptable linking groups include an ester group, an amide group, an imide group, a carbamate group, a carboxyl group, a hydroxyl group, a carbohydrate, a succinimide group (including without limitation, succinimidyl succinate (SS), succinimidyl propionate (SPA), succinimidyl carboxymethylate (SCM), succinimidyl succinamide (SSA) and N-hydroxy succinimide (NHS)), an epoxide group, an oxycarbonylimidazole group (including without limitation, carbonyldimidazole (CDI)), a nitro phenyl group (including without limitation, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In certain embodiments, the linking group is a succinimide group. In one embodiment, the linking group is NHS.

The compstatin analogs of the present invention can alternatively be coupled directly to PEG (i.e., without a linking group) through an amino group, a sulfhydryl group, a hydroxyl group or a carboxyl group. In one embodiment, PEG is coupled to a lysine residue added to the C-terminus of compstatin.

As an alternative to PEGylation, the in vivo clearance of peptides can also be reduced by linking the peptides to certain other molecules or peptides. For instance, certain albumin binding peptides (ABP) display an unusually long half-life of 2.3 h when injected by intravenous bolus into rabbits (Dennis et al., 2002, *J Biol Chem.* 277: 35035-35043). A peptide of this type, fused to the anti-tissue factor Fab of D3H44 enabled the Fab to bind albumin while retaining the ability of the Fab to bind tissue factor (Nguyen et al., 2006, *Protein Eng Des Set* 19: 291-297.). This interaction with albumin resulted in significantly reduced in vivo clearance and extended half-life in mice and rabbits, when compared with the wild-type D3H44 Fab, comparable with those seen for PEGylated Fab molecules, immunoadhesins, and albumin fusions. WO2010/127336 sets forth suitable synthesis strategies utilizing an ABP as well as an albumin-binding small molecule (ABM), and optionally employing a spacer or linker between the components. Those procedures resulted in the production of conjugates of ABP- and ABM-compstatin analogs capable of inhibiting complement activation and also exhibiting extended in vivo survival. Example 1 herein describes the use of those and other procedures with a higher affinity albumin-binding small molecule, ABM2, to generate a compstatin analog-ABM2 C-terminal conjugate utilizing a linker molecule. Example 1 further describes the production of N-terminal conjugates of certain compstatin analogs with three different albumin-binding small molecules, ABM, ABM0 and ABM2 using direct attachment without a linker. Such conjugates, whether C-terminal, N-terminal direct or via a spacer or linker, display C3 binding and complement-inhibiting activity comparable to or exceeding that of the unconjugated analogs, as well as favorable in vivo retention.

The complement activation-inhibiting activity of compstatin analogs, peptidomimetics and conjugates may be tested by a variety of assays known in the art. In certain embodiments, the assays described in the Examples are utilized. A non-exhaustive list of other assays is set forth in U.S. Pat. No. 6,319,897, WO99/13899, WO2004/026328, WO2007/062249 and WO2010/127336, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which compstatin itself is utilized, as known in the art. Such uses include, but are not limited to: (1) inhibiting complement activation in the serum, and on cells, tissues or organs of a patient (human or animal), which can facilitate treatment of certain diseases or conditions, including but not limited to, age-related macular degeneration, rheumatoid arthritis, spinal cord injury, Parkinson's disease, Alzheimer's disease, cancer, sepsis, paroxysmal nocturnal hemoglobinuria, psoriasis and respiratory disorders such as asthma, chronic obstructive pulmonary disease (COPD), allergic inflammation, emphysema, bronchitis, bronchiecstasis, cystic fibrosis, tuberculosis, pneumonia, respiratory distress syndrome (RDS—neonatal and adult), rhinitis and sinusitis; (2) inhibiting complement activation that occurs during cell or organ transplantation, or in the use of artificial organs or implants (e.g., by time-restricted systemic administration before, during and/or after the procedure or by coating or otherwise treating the cells, organs, artificial organs or implants with a peptide of the invention); (3) inhibiting complement activation that occurs during extracorporeal shunting of physiological fluids (blood, urine) (e.g., by time-restricted systemic administration before, during and/or after the procedure or by coating the tubing through which the fluids are shunted with a peptide of the invention); and (4) in screening of small molecule libraries to identify other inhibitors of compstatin activation (e.g., liquid- or solid-phase high-throughput assays designed to measure the ability of a test compound to compete with a compstatin analog for binding with C3 or a C3 fragment).

To implement one or more of the utilities mentioned above, another aspect of the invention features pharmaceutical compositions comprising the compstatin analogs or conjugates described and exemplified herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

A particular compstatin analog of the invention may be selected for a particular formulation on the basis of its solubility characteristics. As mentioned above, analogs that are highly soluble in water or buffered saline may be particularly suitable for systemic injection because the injection volume can be minimized. By comparison, analogs with high water solubility and lower solubility in buffered saline could produce a more long-lasting gel, suspension or precipitate for topical application or local injection, such as intraocular injection. Thus, for illustrative purposes and not intended to be limiting, Cp30 (SEQ ID NO:7) could be selected for pharmaceutical formulations to be administered by systemic injection, while Cp40 (SEQ ID NO:18) may be selected for formulations for intravitreal injection. Notably, Cp40 (SEQ ID NO:18) has been demonstrated to be available orally and via subcutaneous or intramuscular injection, which provides important additional avenues for delivery, as discussed below.

The formulations of the pharmaceutical compositions may be prepared by any method known or hereafter developed in the art of pharmaceutical technology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically-acceptable carrier" means a chemical composition with which a compstatin analog may be combined and which, following the combination, can be used to administer the compstatin analog to an individual.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention may be administered to deliver a dose of between 1 ng/kg and 100 mg/kg body weight as a single bolus, or in a repeated regimen, or a combination thereof as readily determined by the skilled artisan. In certain embodiments, the dosage comprises at least 0.1 mg/kg, or at least 0.2 mg/kg, or at least 0.3 mg/kg, or at least 0.4 mg/kg, or at least 0.5 mg/kg, or at least 0.6 mg/kg, or at least 0.7 mg/kg, or at least 0.8 mg/kg, or at least 0.9 mg/kg, or at least 1 mg/kg, or at least 2 mg/kg, or at least 3 mg/kg, or at least 4 mg/kg, or at least 5 mg/kg, or at least 6 mg/kg, or at least 7 mg/kg, or at least 8 mg/kg, or at least 9 mg/kg, or at least 10 mg/kg, or at least 15 mg/kg, or at least 20 mg/kg, or at least 25 mg/kg, or at least 30 mg/kg, or at least 35 mg/kg, or at least 40 mg/kg, or at least 45 mg/kg, or at least 50 mg/kg, or at least 55 mg/kg, or at least 60 mg/kg, or at least 65 mg/kg, or at least 70 mg/kg, or at least 75 mg/kg, or at least 80 mg/kg, or at least 85 mg/kg, or at least 90 mg/kg, or at least 95 mg/kg, or at least 100 mg/kg, on a daily basis or on another suitable periodic regimen. In a particular embodiment, the dosage is between about 0.5 mg/kg and about 20 mg/kg, or between about 1 mg/kg and about 10 mg/kg, or between about 2 mg/kg and about 6 mg/kg.

In one embodiment, the invention envisions administration of a dose that results in a serum concentration of the compstatin analog between about 0.01 µM and about 30 µM in an individual. In certain embodiments, the combined dose and regimen will result in a serum concentration, or an average serum concentration over time, of the compstatin analog of at least about 0.01 µM, or at least about 0.02 or at least about 0.03 µM, or at least about 0.04 µM in or at least about 0.05 µM, or at least about 0.06 µM, or at least about 0.07 µM, or at least about 0.08 µM, or at least about 0.09 µM, or at least about 0.1 µM, 0.11 µM, or at least about 0.12 µM, or at least about 0.13 µM, or at least about 0.14 µM, or at least about 0.15 µM, or at least about 0.16 µM, or at least about 0.17 µM, or at least about 0.18 µM, or at least about 0.19 µM, or at least about 0.2 µM, or at least about 0.3 µM, or at least about 0.4 µM, or at least about 0.5 µM, or at least about 0.6 µM, or at least about 0.7 µM, or at least about 0.8 µM, or at least about 0.9 µM, or at least about 1 µM or at least about 1.5 µM, or at least about 2 µM, or at least about 2.5 µM, or at least about 3 µM, or at least about 3.5 µM, or at least about 4 µM, or at least about 4.5 µM, or at least about 5 µM, or at least about 5.5 µM, or at least about 6 µM, or at least about 6.5 µM, or at least about 7 µM, or at least about 7.5 µM, or at least about 8 µM, or at least about 8.5 µM, or at least about 9 µM, or at least about 9.5 µM, or at least about 10 µM, or at least about 10.5 µM, or at least about 11 µM or at least about 11.5 µM, or at least about 12 µM, or at least about 12.5 µM, or at least about 13 µM, or at least about 13.5

µM, or at least about 14 µM, or at least about 14.5 µM, or at least about 15 µM, or at least about 15.5 µM, or at least about 16 µM, or at least about 16.5 µM, or at least about 17 µM, or at least about 17.5 µM, or at least about 18 µM, or at least about 18.5 µM, or at least about 19 µM, or at least about 19.5 µM, or at least about 20 µM, or at least about 20.5 µM, or at least about 21 µM or at least about 21.5 µM, or at least about 22 µM, or at least about 22.5 µM, or at least about 23 µM, or at least about 23.5 µM, or at least about 24 µM, or at least about 24.5 µM, or at least about 25 µM, or at least about 25.5 µM, or at least about 26 µM, or at least about 26.5 µM, or at least about 27 µM, or at least about 27.5 µM, or at least about 28 µM, or at least about 28.5 µM, or at least about 29 µM, or at least about 29.5 µM, or at least about 30 µM. In certain embodiments, the combined dose and regimen will result in a serum concentration, or an average serum concentration over time, of the compstatin analog of up to about 0.1 µM, or up to about 0.11 µM, or up to about 0.12 µM, or up to about 0.13 µM, or up to about 0.14 µM, or up to about 0.15 µM, or up to about 0.16 µM, or up to about 0.17 µM, or up to about 0.18 µM, or up to about 0.19 µM, or up to about 0.2 µM, or up to about 0.3 µM, or up to about 0.4 µM, or up to about 0.5 µM, or up to about 0.6 µM, or up to about 0.7 µM, or up to about 0.8 µM, or up to about 0.9 µM, or up to about 1 µM or up to about 1.5 µM, or up to about 2 µM, or up to about 2.5 µM, or up to about 3 µM, or up to about 3.5 µM, or up to about 4 µM, or up to about 4.5 µM, or up to about 5 µM, or up to about 5.5 µM, or up to about 6 µM, or up to about 6.5 µM, or up to about 7 µM, or up to about 7.5 µM, or up to about 8 µM, or up to about 8.5 µM, or up to about 9 µM, or up to about 9.5 µM, or up to about 10 µM, or up to about 10.5 µM or up to about 11 µM or up to about 11.5 µM, or up to about 12 µM, or up to about 12.5 µM, or up to about 13 µM, or up to about 13.5 µM, or up to about 14 µM, or up to about 14.5 µM, or up to about 15 µM, or up to about 15.5 µM, or up to about 16 µM, or up to about 16.5 µM, or up to about 17 µM, or up to about 17.5 µM, or up to about 18 µM, or up to about 18.5 µM, or up to about 19 µM, or up to about 19.5 µM, or up to about 20 µM, or up to about 20.5 µM or up to about 21 µM or up to about 21.5 µM, or up to about 22 µM, or up to about 22.5 µM, or up to about 23 µM, or up to about 23.5 µM, or up to about 24 µM, or up to about 24.5 µM, or up to about 25 µM, or up to about 25.5 µM, or up to about 26 µM, or up to about 26.5 µM, or up to about 27 µM, or up to about 27.5 µM, or up to about 28 µM, or up to about 28.5 µM, or up to about 29 µM, or up to about 29.5 µM, or up to about 20 µM.

Suitable ranges include about 0.1 to about 30 µM, or about 1 to about 29 µM, or about 2 to about 28 µM, or about 3 to about 27 µM, or about 4 to about 26 µM, or about 5 to about 25 µM, or about 6 to about 24 µM, or about 7 to about 23 µM, or about 8 to about 22 µM, or about 9 to about 21 µM, or about 10 to about 20 µM, or about 11 to about 19 µM, or about 12 to about 18 µM, or about 13 to about 17 µM, or about 1 to about 5 µM, or about 5 to about 10 µM, or about 10 to about 15 µM, or about 15 to about 20 µM, or about 20 to about 25 µM, or about 25 to about 30 µM. While the precise dosage administered will vary depending upon any number of factors, including but not limited to, the type of patient and type of disease state being treated, the age of the patient and the route of administration, such dosage is readily determinable by the person of skill in the art.

The pharmaceutical composition can be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the patient, as described above.

Pharmaceutical compositions that are useful in the methods of the invention may be administered systemically in oral, parenteral, ophthalmic (including intravitreal), suppository, aerosol, topical, transdermal or other similar formulations. Such pharmaceutical compositions may contain pharmaceutically acceptable carriers and other ingredients known to enhance and facilitate drug administration. Other formulations, such as nanoparticles, liposomes, resealed erythrocytes, and immunologically based systems may also be used to administer a compstatin analog according to the methods of the invention.

As used herein, "oral administration" or "enteral administration" of a pharmaceutical composition includes any route of administration characterized by introduction into the gastrointestinal tract. Such administration includes feeding by mouth as well as orogastric or intragastric gavage. Such administration also may include sublingual, buccal, intranasal, pulmonary or rectal administration, among other routes known in the art.

Formulations of a pharmaceutical composition suitable for oral administration comprise the active ingredient combined with a pharmaceutically acceptable carrier, in a variety of dosage forms, including but not limited to pills, tablets, granules, powders, capsules, dispersions, suspensions, solutions, emulsions, microemulsions, gels and films, to name a few. Such dosage forms typically include carriers and excipients to facilitate formulation and delivery of the active ingredients.

The pharmaceutically acceptable carriers are selected from proteins, carbohydrates, lipids, organic and inorganic molecules, and combinations thereof. The active ingredients can be combined with the carrier in an appropriate diluent to form a solution or a suspension. Such liquid formulations can be viscous or non-viscous depending on the amount and the carrier used. The liquid formulations can be used directly or can be further formulated into an appropriate capsule, gel capsule or solid by methods know to those skilled in the art. Alternatively, solid formulations can be made by combining solid components. Such solid formulations can be used as a powder or formulated into granules, capsules, tablets or films any one of which can be made as a time release formulation.

Suitable proteins for use as carriers in oral dosage forms include milk proteins such as casein, sodium caseinate, whey, reduced lactose whey, whey protein concentrate, gelatin, soy protein (isolated), brown algae protein, red algae protein, baker's yeast extract and albumins. Suitable carbohydrates include celluloses such as methylcellulose, sodium carboxymethylcellulose, carboxymethylcellulose, hydroxypropylcellulose, hydroxypropylmethylcellulose, cellulose acetate and ethyl cellulose, starches such as cornstarch, potato starch, tapioca starch, wheat starch, acid modified starch, pregelatinized starch and unmodified starch, alginates such as ammonium alginate, sodium alginate, and calcium alginate, glutens such as corn gluten and wheat gluten, gums such as acacia (gum Arabic), gum ghatti, guar gum, karaya gum (sterculia gum) and gum (tragacanth), insoluble glucose isomerase enzyme preparations, sugars such as corn sugar, invert sugar, corn syrup, high fructose corn syrup, and sodium gluconate. Suitable lipids include tocopherols such as a-tocopherol acetate, short-, medium- and long-chain fatty acids and esters thereof, fatty alcohols and ethers thereof, oils such as coconut oil (refined), soybean oil (hydrogenated) and rapeseed oil, aluminum palmitate, dilauryl thiodipropionate, enzyme-modified lecithin, calcium stearate, enzyme-modified fats, glyceryl palmitostereate, lecithin, mono- and diglycerides, glycerin and waxes such as beeswax (yellow and white), candelilla wax and carnauba wax and vegetable oil. Suitable organic and inorganic substances include methyl and vinyl pyrrolidones such as polyvinylpyrrolidone, methylsulfonyl methane, dimethylsulfoxide and related compounds, hydroxy and polyhydroxy acids such as polylactic acid, among many others.

In some embodiments, controlled release forms may be prepared to achieve a sustained, or location-specific liberation of the compstatin analog in the digestive tract in order to improve absorption and prevent certain forms of metabolism. For example, acid-resistant coatings of tablet or acid-resistant capsule materials may be used to prevent a release of compstatin analogs in the stomach and protect the compound from metabolism by gastric enzymes. Suitable materials and coatings to achieve controlled release after passage of the stomach are primarily composed of fatty acids, waxes, shellac, plastics and plant fibers and include, but are not limited to, methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate, sodium alginate or stearic acid. Sustained release in the gastrointestinal tract can for example be achieved by embedding compstatin analogs in a matrix of insoluble substances such as various acrylics, chitin and others. Methods to prepare such formulations are known to those skilled in the art.

Compstatin may be formulated into suppositories or clysters for rectal, vaginal or urethral administration. For this purpose, compstatin analogs can be dissolved or suspended in a greasy base carrier such as cocoa butter that is solid or semi-solid at room temperature but melts at body temperature or in a water-soluble solid base such as polyethylene glycol or glycerin (made from glycerol and gelatin). Other excipients may be added to improve the formulation, and suppositories will be shaped in a form that facilitates administration. In other embodiments, liquid suppositories consisting of compstatin analogs dissolved or suspended in a liquid carrier suitable for rectal delivery to be applied with a small syringe may be used.

For the treatment of chronic or acute lung conditions in which complement activation is implicated, a preferred route of administration of a pharmaceutical composition is pulmonary administration. Accordingly, a pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, including replacement pulmonary surfactant, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intraarticular, intravitreal, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution can be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa.

Methods:

Another aspect of the invention features methods of regulating complement activation. In general, the methods comprise contacting a medium in which regulation of complement activation is desired with a compstatin analog of the present invention, wherein the contacting results in regulation of complement activation in the medium. The medium can be any medium in which regulation of complement activation is desired. In certain embodiments, the medium includes cells or tissues of an organism, including (1) cultured cells or tissues, (2) cells or tissues within the body of a subject or patient, and (3) cells or tissues that have been removed from the body of one subject and will be replaced into the body of the same patient (e.g., extracorporeal shunting of blood or autologous transplantation) or transferred to another patient. In connection with the latter embodiment, the medium may further comprise a biomaterial, such as tubing, filters or membranes that contact the cells or tissues during extracorporeal shunting. Alternatively, the medium may comprise biomaterials that are implanted into a subject.

In certain embodiments, the methods of regulating complement activation apply to living patients or subjects and comprise part or all of a method of treating the patient for a pathological condition associated with complement activation, particularly AP-mediated complement activation. Many such pathological conditions are known in the art (see, e.g., Holers, 2008, supra) and include, but are not limited to, as atypical hemolytic uremic syndrome (aHUS), dense deposit disease, age-related macular degeneration (AMD), paroxysomal nocturnal hemoglobinuria (PNH), cold agglutinin disease (CAD) rheumatoid arthritis (RA), systemic lupus erythematosus (SLE), several autoimmune and auto-inflammatory kidney diseases, autoimmune myocarditis, multiple sclerosis, traumatic brain and spinal cord injury, intestinal and renal ischemia-reperfusion (IR) injury, spontaneous and recurrent pregnancy loss, anti-phospholipid syndrome (APS), Alzheimer's disease, asthma, anti-nuclear cytoplasmic antigen-associated pauci-immune vasculitis (Wegener's syndrome), non-lupus autoimmune skin diseases such as pemphigus, bullous pemphigoid, and epidermolysis bullosa, post-traumatic shock, certain forms of cancer, and atherosclerosis. In particular embodiments, the pathological condition has been associated with mutations and polymorphisms in the gene encoding FH and/or CD46, including but not limited to: AMD, aHUS and membrano-proliferative glomerulonephritis type II (MPGN-II, also referred to as dense deposit disease (DDD)). In other embodiments, the comstatin analogs of the present invention are suitable for use as a substitute for Eculizumab or TT30 in treatment of diseases for which those agents are currently prescribed, or for which they are being developed in preclinical and clinical studies. Those diseases include, but are not limited to, aHUS, PNH, CAD and AMD.

The treatment methods typically comprise (1) identifying a subject with a disease or condition treatable by regulation of complement activation as described hereinabove, and (2) administering to the subject an effective amount of a compstatin analog of the invention using a treatment regimen and duration appropriate for the condition being treated. Development of appropriate dosages and treatment regimens will vary depending upon any number of factors, including but not limited to, the type of patient and type of disease state being treated, the age of the patient and the route of administration. The skilled artisan is familiar with the design of dosage regimens that take such variables into account. For instance, it will be apparent to the skilled artisan that oral administration of a compstatin analog of the invention will require a higher initial dosage, due to the lesser bioavailability from that route as compared with, e.g., intravenous injection.

The following examples are provided to describe the invention in greater detail. They are intended to illustrate, not to limit, the invention.

Example 1

This example describes the synthesis of compstatin analogs with N-terminal modifications, and conjugates of certain analogs to albumin-binding small molecules.

Chemicals.

Rink amide MBHA resin, Oxyma and the following Fmoc-amino acids were obtained from Novabiochem (San Diego, Calif.): Ile, Cys(Trt), Val, Tyr(tBu), Gln(Trt), Asp (OtBu), Trp(Boc), Gly, Sar, Ala, MeAla, His(Trt), Arg(Pbf), MeIle, Phe, MePhe and D-Cha. DIC and Fmoc-Trp(Me)-OH were purchased from AnaSpec (San Jose, Calif.). HOAt was purchased from Advanced ChemTech (Louisville, Ky.). NMP and DCM were obtained from Fisher Scientific (Pittsburgh, Pa.). All other chemical reagents for synthesis were purchased from Sigma-Aldrich (St. Louis, Mo.) and used without further purification.

Peptide Synthesis and Purification.

All peptides were synthesized manually by Fmoc solid-phase methodology using DIC and Oxyma as coupling reagents. The following procedures were used for the synthesis of the linear peptides: Rink amide MBHA resin (0.59 mmol/g) was placed into a peptide synthesis glass vessel equipped with frits on the bottom and swollen in DCM for 30 min. After removal of the Fmoc protecting group (25% piperidine in NMP, 5 and 10 min), the resin was washed 7 times with NMP and twice with DCM, and the individual amino acids were coupled to the resin. For each coupling, 3 equivalents of the amino acid, HOAt, and DIC were used, with 10 min preactivation in NMP. All couplings were performed for 1 h and monitored by either the Kaiser test or the chloranil test. In case of a positive test result, the coupling was repeated until a negative test result was observed. The synthesis was stopped after the coupling of Cys in position 1. Then the resin was split in HSW polypropylene syringe with frits on the bottom (Torviq, Niles, Mich.) and coupling of addition amino acids was coupled using method reported previously.

Upon completion of the solid phase synthesis, the resin was washed four times with NMP, DCM, and DCM/diethylether (1:1), and dried under high vacuum for 4 h. The peptides were cleaved from the resin with a mixture of 94% TFA, 2.5% water, and 2.5% EDT and 1% TIPS for 2 h. After evaporation of the TFA under vacuum, the peptides were precipitated and washed three times with cold diethyl ether. The liquid was separated from the solid by centrifugation and decanted. The crude peptides were dried in vacuum and dissolved in 30% acetonitrile. The pH of solution was adjusted to 8-9 using concentrated ammonium hydroxide. To the solution was added diluted hydrogen peroxide (1:100, 2 eq.) with vigorous stirring. The cyclization was monitored by using MALDI-TOF. Once the reaction was completed, the solution was supplemented with TFA to lower the pH to 2. And the solution was lyophilized. The crude peptide was purified with RP-HPLC as described previously (Qu et al., 2011, supra). The purified peptides were >95% pure as determined by analytical RP-HPLC (Phenomenex 00G-4041-E0 Luna 5μ C18 100A column, 250×4.60 mm; Phenomenex, Torrance, Calif.). The mass of each peptide was confirmed using Waters MALDI micro MX instruments or Synapt HDMS.

Certain of the compstatin analogs were conjugated to an albumin-binding small molecule, examples of which are shown below.

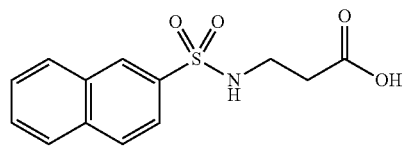
ABM

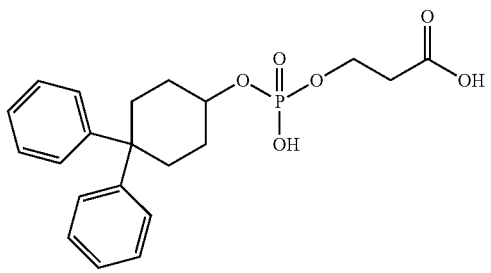
ABM0

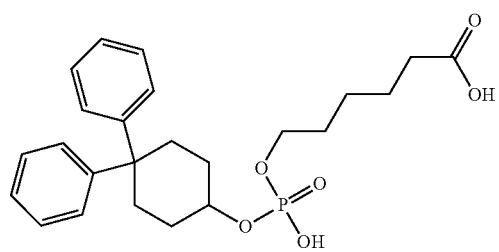
ABM2

In one construct, ABM2 was coupled to the C-terminus of peptide Cp30 (SEQ ID NO:7; Table 1 below) via a mini-PEG-3 spacer in accordance with the methods described in WO2010/127336.

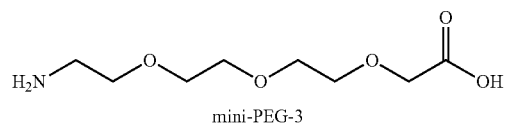 [SMILES: NCCOCCOCCOCC(=O)O]
mini-PEG-3

In other constructs, ABM, ABM0 or ABM2 were coupled to the N-terminus of CP20 (SEQ ID NO:3) or CP40 (SEQ ID NO:18) without a spacer.

Example 2

Compstatin analogs synthesized by the methods described in Example 1 were measured for C3 binding and complement-inhibitory activity.

Materials and Methods:

Inhibition of Complement Activation.

The ability of the compstatin analogs to inhibit the activation of the classical pathway of complement was assessed by ELISA as described elsewhere (Katragadda et al., 2006, supra; Mallik et al., 2005, supra). The percent inhibition was plotted against the peptide concentration, and the resulting data set was fitted to the logistic dose-response function using Origin 8.0 software. $IC_{50}$ values were obtained from the fitted parameters that produced the lowest $\chi 2$ value. Each analog was assayed at least three times.

SPR Analysis.

The interaction of the compstatin analogs with C3b was characterized using a Biacore 3000 instrument (GE Healthcare, Corp., Piscataway, N.J.). The running buffer was PBS, pH 7.4 (10 mM sodium phosphate, 150 mM NaCl) with 0.005% Tween-20. Biotinylated C3b was captured site-specifically on a streptavidin chip at about 3000 and 5000 RU density; two untreated flow cells were used as reference surface. For kinetic analysis, sets of five increasing concentrations of a particular compound were injected over the chip surface one after the other in a single cycle. Three-fold dilution series (0.49-40 nM were injected at 3 µl/min; each injection was done for 2 min, allowing every time the peptide to dissociate for 5 min before the next injection started. After the end of the last injection, 40 min of dissociation time was allowed. Peptide 4 (1 MeW) was included in each experimental series as an internal control and reference. Data analysis was performed using Scrubber (BioLogic Software, Campbell, Australia) and BiaEvaluation (GE Healthcare, Corp., Piscataway, N.J.). The signals from an untreated flow cell and an ensemble of buffer blank injections were subtracted to correct for buffer effects and injection artifacts. Processed biosensor data were globally fitted to a 1:1 Langmuir binding model (kindly provided by GE Healthcare), and the equilibrium dissociation constant ($K_D$) was calculated from the equation $K_D=k_d/k_a$. Each assay was performed at least twice.

Docking Peptides to C3c.

AutoDock Vina (Trott and Olson, 2010) was used for docking studies. With exception of the backbone of the cyclic core region that can only be handled as rigid by Vina, all other parts of the peptides (terminal residues, side chains) were defined as flexible during the docking runs. The residues of C3c near the N-terminus of analog Cp20 (SEQ ID NO:3) (i.e., Asp349, Lys386, Ser388, Asn390, Ser437, Asn452, Leu454, Asp491 and Leu492) were defined as flexible for the docking experiments in order to allow for more reasonable interactions between the extended N-terminus of these peptides and C3c. The only exception was peptide 19, the N-terminus of which does not extended as other peptides; the binding site area on C3c therefore remained rigid in the docking of peptide 19. Initial structures of all peptides were manually built in PyMol based on the C3c-bound structure of 4W9A. AutoDockTools was used to define the binding pocket and prepare the initial structures of C3c and all peptides from the pdb format into the input format of Vina (pdbqt).55 In the comparison plot of computational versus experimental binding free energy ($\Delta G$), the experimental $\Delta G$ was calculated from the affinity values determined by SPR as $\Delta G=RT \ln(KD)$, with R=1.986 cal $K^{-1}$ $mol^{-1}$ and T=293.15 K.

Results:

Structure/Activity of N-Terminal Extensions.

Using a molecular modeling approach, the early compstatin analog 4W9A was replaced by Cp20 (SEQ ID NO:3) in the co-crystal structure with the target fragment C3c. Computational analysis of this complex confirmed that the methyl group of Sar8 forms a contact with oxygen atom of G489 in C3c (distance ~4.0 Å). Yet analysis of the binding site also revealed the existence of a hydrophobic area on C3c that may be exploited via N-terminal extension of the peptide ligand. While not buried in the binding pocket of C3c, the N-terminus of compstatin has previously been protected by an acetyl moiety primarily to improve peptide stability; however, such capping also had a beneficial effect on the inhibitory potency. Based on the current lead compound Cp20 (SEQ ID NO:3), the effect of replacing the N-terminal acetyl moiety on target binding was evaluated (Table 1). For this purpose, analogs were subjected to quantitative kinetic profiling for their binding to C3b and compared to the clinically used analog 4 (1 MeW) and to Cp20 (SEQ ID NO:3) (Table 1, FIG. 1). Indeed, substitution of the terminal acetyl with a shorter methyl group (peptide 1) led to a drop in affinity by almost an order of magnitude, below that of 4 (1 MeW), thereby confirming the advantage of N-terminal capping. In contrast, capping with a glycine residue (peptide 2) improved the dissociation rate ($k_d$) yet slightly lowered the association rate ($k_a$), leading to only a very small net change in affinity (compared to Cp20 (SEQ ID NO:3)). N-methylation of Gly to Sar (peptide 3) restored the association properties while retaining the beneficial dissociation value, which produced a compound with significantly improved affinity ($K_D$=1.6 nM; Table 1).

To further explore the benefit of N-terminal optimization, additional Cp20 (SEQ ID NO:3)-based analogs with natural (peptides 4-8), methylated (peptides 9-13) and D-amino acids (peptides 14-18) at position Xaa0 (FIG. 1B; Table 1) were screened. The set included representative hydrophobic, hydrophilic, and charged side chains. All tested compounds showed strong binding ($K_D$<20 nM), with the $k_a$ values ($1-4\times10^6 M^{-1}s^{-1}$) showing less variability than $k_d$ values ($1-25\times10^{-3}$ $s^{-1}$) across the entire panel (Table 1, FIG. 1B). All analogs followed a 1:1 Langmuir kinetic model when screened for binding to C3b, thereby strongly supporting the presence of a single high-affinity binding site. In general, D-amino acids with hydrophobic side chains appeared to be favored over the acetyl (Ac) moiety of Cp20 (SEQ ID NO:3). Among those, peptide 14 with a DTyr at that position was the most potent, with a subnanomolar affinity ($K_D$=0.5 nM; Table 1) and the slowest dissociation rate of the panel. The affinity of peptides in which Ac was replaced by other amino acids fell between that of peptides 1 and 14, with most analogs clustering around the profile of Cp20 (SEQ ID NO:3) (FIG. 1B). Tyrosine appears generally preferred since all peptides with N-terminal Tyr, its O-methyl analog and its D-isoform ranked among the best binders with affinities around or below 1 nM. In contrast, residues with shorter side chains like Gly, Thr, or Ala derivatives seemed less favorable and did not improve the affinity compared to Cp20 (SEQ ID NO:3). Thus, replacement of the capping Xaa0 residue appears to be well tolerated for a wide range of amino acid residues with varying properties, from hydrophobic to charged.

TABLE 1

Evaluation of kinetic parameters and inhibitory potency for a series of compstatin analogs (Xaa0-Xaa1-[Cys-Val-Trp(Me)-Gln-Asp-Trp-Sar-Ala-His-Arg-Cys]-mIle-NH$_2$) (SEQ ID NO: 4) with modifications at the N-terminus. $k_a$: association rate; $k_d$: dissociation rate; $K_D$: binding constant from SPR; IC$_{50}$, peptide concentration to reach 50% inhibition of classical pathway complement activation. ND: not determined.

| Peptide | SEQ ID NO: | Xaa0 | Xaa1 | $k_a$ ($10^6$/Ms) | $k_d$ ($10^{-3}$/s) | $K_D$ (nM) | IC$_{50}$ (nM) |
|---|---|---|---|---|---|---|---|
| 4(1MeW)[a] | 2 | — | — | 1.1 ± 0.1 | 11.3 ± 0.9 | 10.3 ± 1.5 | 132 ± 7 |
| Cp20[b] | 3 | Ac | Ile | 1.9 | 4.0 | 2.4 | |
| 1 | 5 | Me | Ile | 1.3 ± 0.3 | 24.8 ± 7.3 | 18.6 ± 3.5 | 180 ± 17 |
| 2 | 6 | Gly | Ile | 1.2 ± 0.3 | 2.9 ± 0.2 | 2.5 ± 0.5 | 113 ± 16 |
| 3[c] | 7 | Sar | Ile | 1.9 ± 0.5 | 2.9 ± 0.3 | 1.6 ± 0.3 | 82 ± 14 |
| 4 | 8 | Tyr | Ile | 2.1 ± 0.3 | 2.5 ± 0.1 | 1.2 ± 0.1 | 72 ± 10 |

TABLE 1-continued

Evaluation of kinetic parameters and inhibitory potency for a series of compstatin analogs (Xaa0-Xaa1-[Cys-Val-Trp(Me)-Gln-Asp-Trp-Sar-Ala-His-Arg-Cys]-mIle-NH$_2$) (SEQ ID NO: 4) with modifications at the N-terminus. $k_a$: association rate; $k_d$: dissociation rate; $K_D$: binding constant from SPR; IC$_{50}$, peptide concentration to reach 50% inhibition of classical pathway complement activation. ND: not determined.

| Peptide | SEQ ID NO: | Xaa0 | Xaa1 | $k_a$ (10$^6$/Ms) | $k_d$ (10$^{-3}$/s) | $K_D$ (nM) | IC$_{50}$ (nM) |
|---|---|---|---|---|---|---|---|
| 5 | 9 | Phe | Ile | 2.1 ± 0.4 | 3.3 ± 0.3 | 1.6 ± 0.2 | ND |
| 6 | 10 | Arg | Ile | 1.7 ± 0.2 | 2.9 ± 0.2 | 1.7 ± 0.2 | ND |
| 7 | 11 | Trp | Ile | 1.6 ± 0.1 | 3.6 ± 0.2 | 2.2 ± 0.2 | ND |
| 8 | 12 | Thr | Ile | 1.2 ± 0.1 | 3.1 ± 0.2 | 2.6 ± 0.3 | ND |
| 9 | 13 | Tyr(Me) | Ile | 2.3 ± 0.4 | 2.6 ± 0.1 | 1.2 ± 0.2 | ND |
| 10 | 14 | mPhe | Ile | 1.6 ± 0.2 | 2.9 ± 0.3 | 1.8 ± 0.3 | ND |
| 11 | 15 | mVal | Ile | 1.8 ± 0.3 | 3.5 ± 0.6 | 1.9 ± 0.1 | ND |
| 12 | 16 | mIle | Ile | 1.6 ± 0.2 | 3.7 ± 0.3 | 2.4 ± 0.5 | ND |
| 13 | 17 | mAla | Ile | 1.4 ± 0.2 | 3.4 ± 0.3 | 2.5 ± 0.6 | ND |
| 14[c] | 18 | D-Tyr | Ile | 2.8 ± 0.5 | 1.4 ± 0.1 | 0.5 ± 0.1 | 66 ± 8 |
| 15 | 19 | D-Phe | Ile | 2.3 ± 0.3 | 2.6 ± 0.0 | 1.1 ± 0.1 | ND |
| 16 | 20 | D-Trp | Ile | 2.0 ± 0.2 | 2.4 ± 0.1 | 1.2 ± 0.1 | ND |
| 17 | 21 | D-Cha[2] | Ile | 1.8 ± 0.5 | 2.7 ± 0.4 | 1.5 ± 0.2 | ND |
| 18 | 22 | D-Ala | Ile | 1.4 ± 0.3 | 3.4 ± 0.4 | 2.5 ± 0.4 | ND |
| 19 | 23 | Ac | Trp | 3.8 ± 0.3 | 1.7 ± 0.3 | 0.5 ± 0.1 | ND |
| 20 | 24 | Tyr | Gly | 2.1 ± 0.3 | 7.3 ± 1.4 | 3.5 ± 0.3 | ND |

[a] Ac-Ile-[Cys-Val-Trp(Me)-Gln-Asp-Trp-Gly-Ala-His-Arg-Cys]-Thr-NH$_2$ (Katragadda et al., 2006, supra, WO 2007/062249; sometimes referred to herein as "4(1MeW)"); included as a standard in all analyses but does not follow the Cp20 (SEQ ID NO: 3) template.
[b] Base compound for N-terminal modifications; binding/potency values from previous publication (WO2010/127336).
[c] Selected for further testing: peptide 3 - Cp30 (SEQ ID NO: 7); peptide 14 - Cp40 (SEQ ID NO: 18)

Computational Analysis.

Figure 2:
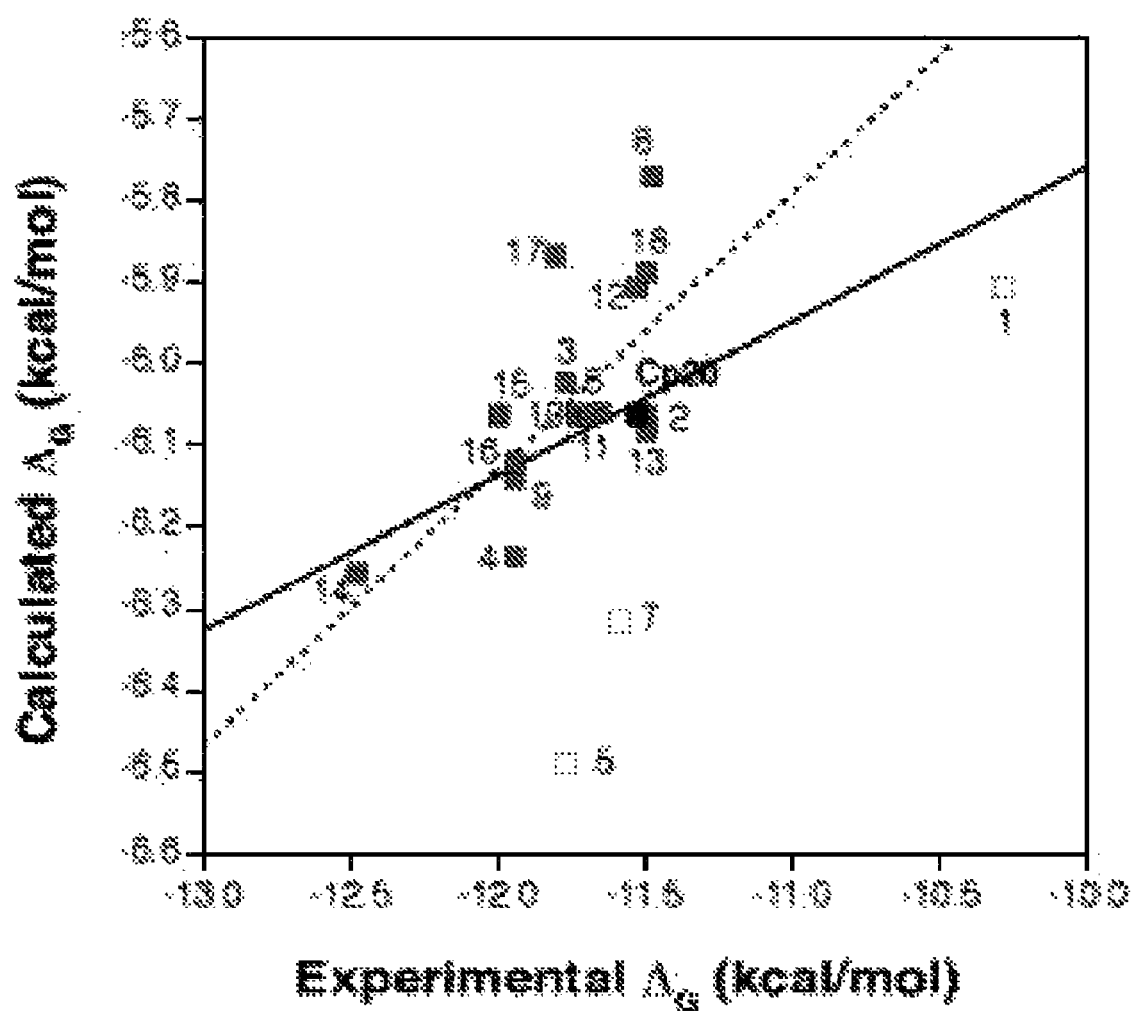
FIG. 2. Correlation between free energy values (ΔG) as calculated from a computational docking experiment between compstatin analogs and C3c (y axis) and from the experimentally determined affinity values of the same analogs for C3b (x axis). Peptide numbers are shown next to each mark on the plot. The correlation over the entire data set is shown as a solid line whereas the dotted line represents the correlation after exclusion of peptides 1, 5 and 7.

Extended docking analyses were performed to provide structural evidence for the observed effects on binding affinity and generate a computational model for predicting novel analogs. Initially, the docking strategy was validated using the data set from the screening of N-terminally modified analogs of Cp20 (SEQ ID NO:3) (peptides 1-18; Table 1). For this purpose, the compounds were prepared in silico, docked into the compstatin binding pocket of human C3c (Janssen et al., 2007, supra), and the binding free energy (ΔG) was calculated and compared to the SPR affinity-derived values by determining the Pearson's coefficient (R, FIG. 2). The overall correlation between experimental and calculated ΔG values was 0.46 based on five independent docking studies over the entire data set (FIG. 2). Out of the 19 analogs in the data sets, three peptides bearing either a very short moiety (methyl; peptide 1) or aromatic natural amino acid (peptides 5 and 7) showed a significantly higher deviation; when these analogs were excluded, the correlation increased to 0.69 (FIG. 2).

Figure 3A:
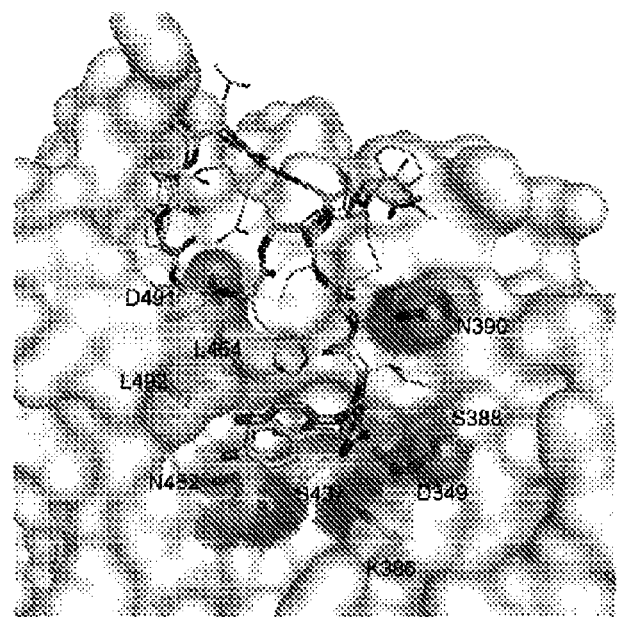
FIG. 3. Docking of compstatin analogs into the binding site of C3c. (A) Docked conformation of peptide 14 (Cp40 (SEQ ID NO:18), cyan in the color figure) and peptide 4 (gray in the color figure) (note in the non-color figure, the aromatic ring of the dY side chain (CP40 (SEQ ID NO:18)) is superimposed in front of the ring of Y (peptide 4) and can be distinguished in that manner). Other D-amino acids have a similar conformation as peptide 14 in the docked models. Side chains of other residues in peptide 4 were omitted for clarity. (B) Docking conformation of peptide 19.

A more detailed analysis of the docked peptides indicated that most of the N-terminally modified compstatin analogs formed additional contacts with a polar area and a shallow pocket on C3c. For example, the polar area involving Asp349, Ser388 and Ser437 of C3c interacts with the N-terminal amino group of DTyr in peptide 14 (FIG. 3A). In contrast, such a polar interaction is not favored for peptides carrying natural amino acid residues at this position, as exemplified for peptide 4, due to a different orientation of the amino group (FIG. 2A). Furthermore, the side chain of the elongated amino acid (DTyr) in peptide 14 forms additional hydrophobic contacts with Leu454 and Leu492 in the shallow extended pocket on C3c. Finally, the hydroxyl group of DTyr formed a weak hydrogen bond with Asn452 of C3c. A combination of those effects is likely to contribute to the observed subnanomolar binding affinity of peptide 14.

Figure 3B:
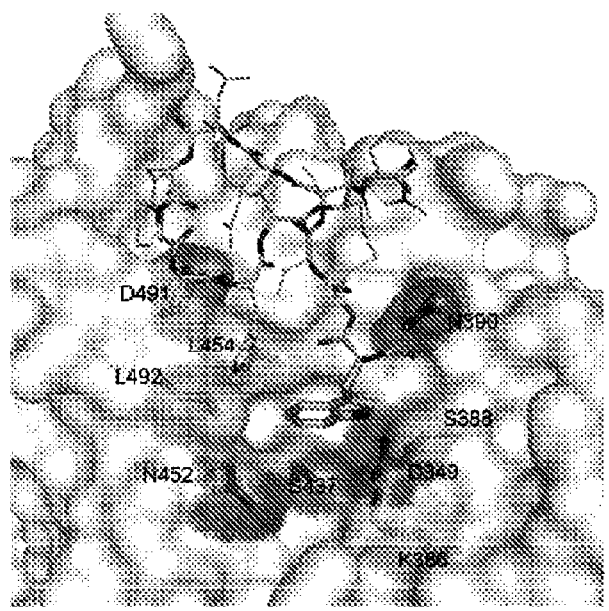

To further explore distinct strategies of addressing the N-terminal pocket, two analogs were designed in which an aromatic residue was located at position Xaa0 or Xaa1 (peptides 19 and 20; Table 1). Based on the computational model developed above, the side chain of the new Trp in peptide 19 was predicted to fit well into the hydrophobic binding pocket (FIG. 3B), whereas a short flexible Gly linker was chosen in peptide 20 to allow a better orientation of the Tyr side chain when compared to the homolog peptide 4. While peptide 20 showed a threefold weaker binding affinity than peptide 4, peptide 19 reached sub-nanomolar binding affinities ($K_D$=0.5 nM; Table 1), making it as potent as peptide 14. Together, these results demonstrate the advantage of a properly oriented hydrophobic residue adjacent to Cys at position 2.

Additional analogs were constructed based on Cp40 (peptide 14, SEQ ID NO:18, Table 1). These are shown in Table 2 below.

TABLE 2

Evaluation of kinetic parameters and inhibitory potency for analogs based on Cp40 (SEQ ID NO: 18) with modifications within the peptide. Numbering within the peptide designation indicates the position relative to compstatin. $k_a$: association rate; $k_d$: dissociation rate; $K_D$: binding constant from SPR; IC$_{50}$, peptide concentration to reach 50% inhibition of classical pathway complement activation.

| Peptide | SEQ ID NO: | $k_a$ (10$^6$/Ms) | $k_d$ (10$^{-3}$/s) | $K_D$ (nM) | IC$_{50}$ (nM) |
|---|---|---|---|---|---|
| Cp40 (peptide 14) | 18 | 2.8 ± 0.6 | 1.3 ± 0.2 | 0.5 ± 0.1 | 0.14 ± 0.05 |
| Cp40 (11Orn) | 25 | 2.5 ± 0.1 | 2.0 ± 0.1 | 0.8 ± 0.1 | 0.22 |
| Cp40 (6Asn) | 26 | 0.9 ± 0.1 | 2.8 ± 0.1 | 3.0 ± 0.4 | 0.26 |
| Cp40 (11Orn 6Asn) | 27 | 2.0 ± 0.4 | 2.8 ± 0.6 | 1.5 ± 0.4 | 0.36 |

[a] ornithine substituted for arginine at position 11.
[b] asparagine substituted for aspartic acid at position 6.

As mentioned above, ABM, ABM0 or ABM2 were coupled without a spacer to the N-terminus of CP20 (SEQ ID NO:3) or CP40 (SEQ ID NO:18) and certain variants thereof. Those analogs displayed binding and complement inhibitory activity in the same range as the Cp40 analog and its derivatives set forth in Table 2.

Example 3

Certain of the compstatin analogs synthesized as described in Example 1 were measured for solubility in water for injection (WFI) and Dulbecco's PBS (DPBS).

Materials and Methods:

Approximately 5 mg of each peptide (acetate form) was weighed out into separate LoBind Eppendorf tubes and 50 μL water for injection (WFI) was added to each tube. Each sample was centrifuged at 13000 rpm for 2 min and diluted for measuring the optical density (OD) at 280 nm using a NanoDrop 2000 spectrophotometer (Thermo Scientific, Wilmington, Del.). Each concentrated sample was diluted 1:20 into Dulbecco's phosphate buffered saline (DPBS, without potassium and calcium; Invitrogen, Carlsbad, Calif.). The samples were monitored for precipitation, and each sample was vortexed for 5 min and centrifuged at 13000 rpm for 2 min. The OD of each DPBS supernatant was measured to determine peptide concentration at saturation.

Results:

While the presence of three acidic or basic residues (Asp6, His10, Arg11) in most compstatin analogs contributes to a generally favorable solubility in aqueous solutions, their zwitterionic nature may negatively affect solubility in buffered solutions. Accordingly, the solubility of selected compounds in two clinically relevant solvents, i.e., water for injection (WFI) and Dulbecco's PBS (DPBS) was evaluated. In addition, the ultra performance liquid chromatography (UPLC) retention time of these peptides on a C18 column was measured to reflect their apparent relative hydrophobicity (Table 3).

TABLE 3

Solubility of peptides in WFI (Water for Injection) and DPBS, and UPLC (Ultra Performance Liquid Chromatography) retention time as an indication of hydrophobicity.

| Peptide | SEQ ID NO: | Solubility (mg/mL)[a] | | Hydophobicity[b] Retention Time (min) |
|---|---|---|---|---|
| | | WFI | DPBS pH 7.4 | |
| 4(1MeW) | 2 | >50 | 3.5 | 5.09 |
| Cp20 | 3 | 13 | 2.7 | 5.33 |
| Cp30 | 7 | >50 | 6.9 | 4.60 |
| Cp40 | 18 | >50 | 0.8 | 4.73 |
| Peptide 19[c] | 23 | ND | <0.2 | ND |

[a]Measured as OD (280 nm) at saturation; WFI = water for injection, DPBS = Dubelcco's phosphate buffered saline
[b]Measured as retention time during UPLC analysis on a C18 column
[c]Peptide 19 could not be solubilized at 100 μM or above in PBS during ELISA studies.

The solubility in WFI was excellent, with values exceeding 50 mg/mL for all compounds with the exception of Cp20 (SEQ ID NO:3). In general, the solubility in DPBS was significantly lower for all analogs. The decreased solubility of Cp20 (SEQ ID NO:3) in both solvents, as compared to 4 (1 MeW), is considered a consequence of its hydrophobicity arising from two N-methylations (positions 8 and 13) and the C-terminal Thr-to-Ile substitution. The replacement of the N-terminal acetyl moiety in 4 (1 MeW) and Cp20 (SEQ ID NO:3) by uncapped amino acid residues induced a significant gain in hydrophilicity for Cp30 (SEQ ID NO:7) and Cp40 (SEQ ID NO:18) and restored their high solubility in WFI (>50 mg/mL). However, the incorporation of a hydrophobic DTyr at its N-terminus negatively impacted the solubility of Cp40 (SEQ ID NO:18) (0.8 mg/mL) in DPBS. In contrast, the presence of a small N-terminal Sar in Cp30 (SEQ ID NO:7) largely improved its solubility in DPBS (6.9 mg/mL), rendering this peptide almost twice as soluble as the clinically-used 4 (1 MeW) analog.

Example 4

Certain of the compstatin analogs synthesized as described in Example 1 were measured for plasma stability and plasma protein binding in human plasma.

Materials and Methods:

Plasma Stability.

Fresh human plasma containing lepirudin (3.75 units/ml) was incubated at 37° C. with Cp30 (SEQ ID NO:7), Cp40 (SEQ ID NO:18) or control peptide 2B at a final concentration of 20 μM each. Samples of 100 μL were taken for solid phase extraction. A 96-well plate HLB Oasis 30 μm 10 mg (Waters, Milford, Mass.) was employed for extraction. The SPE material was conditioned by addition of 500 μL each of methanol and ACN followed by addition of 500 μL of milli-Q water. Sample was diluted 1:1 with 4% $H_3PO_4$. After loading the sample, washing was carried out twice with 500 μL of 10% ACN in 0.1% formic acid. Sample was eluted with 200 μL of 65% ACN in 0.1% formic acid and collected in the Eppendorf LoBind collection plate. Sample for UPLC-MS was diluted 1:10 in milli-Q water with 0.1% formic acid. Cp20 (SEQ ID NO:3) was spiked in each sample before SPE as an internal standard.

Plasma Protein Binding.

Cp30 (SEQ ID NO:7) was spiked in 500 μL of fresh human plasma containing lepirudin (3.75 units/ml) so that the final peptide concentration was 20 μM (C3: 1.2 mg/mL, 6.4 μM). A control sample was prepared in the same way using Cp30 (SEQ ID NO:7) and milli-Q water to determine the area of peptide in UPLC-MS at 1 μM. The plasma sample was equilibrated at room temperature for 10 min. Then, 500 μL of 30% PEG in milli-Q water (MW3350) was slowly added to the plasma sample while mixing. The mixture was centrifuged at 14000 rpm for 10 min to separate the supernatant. The pellet was dissolved in 1000 μL of FPLC buffer A and separated by FPLC using Mono Q 5/5 column and fractions was collected at 1 mL per tube 0.5 mL of each fraction was mixed with same volume off 4% $H_3PO_4$ for SPE and UPLC-MS analysis.

UPLC-MS Analysis.

UPLC-MS analysis was performed on a SYNAPT HDMS (Waters, Milford, Mass.) equipped with an ESI source controlled by MassLynx 4.1 software (Waters). Each sample was injected in quadruplicates. An online ACQUITY UPLC (Waters) system was used for peptide separation by reversed-phase liquid chromatography. The capillary voltage was 3.2 kV, the cone voltage was 30 V and the source temperature was 120° C. [Glu1]-fibrinogen peptide was used for lock-mass correction with a sampling rate of 30 s. Mass spectra were acquired in positive mode over an m/z range 200-2000 Da at scan rate 1 s. The presence of the analyte was confirmed by retention time and mass. Selectivity was studied by analysis of blank plasma sample and pure peptides to determine the presence of any interference coeluting with the analyte. After injection, analytes were separated on a 1.7 μm UPLC BEH130 C18 column (Water, 2.1 μm×150 mm, part number 186003556). The analytical column temperature was held at 40° C. Peptides were separated at flow rate 0.3 mL/min. The gradient was linear 10-60% B (0.1% formic acid in acetonitrile) over 8 min.

Results:

Plasma Stability.

Figure 4:
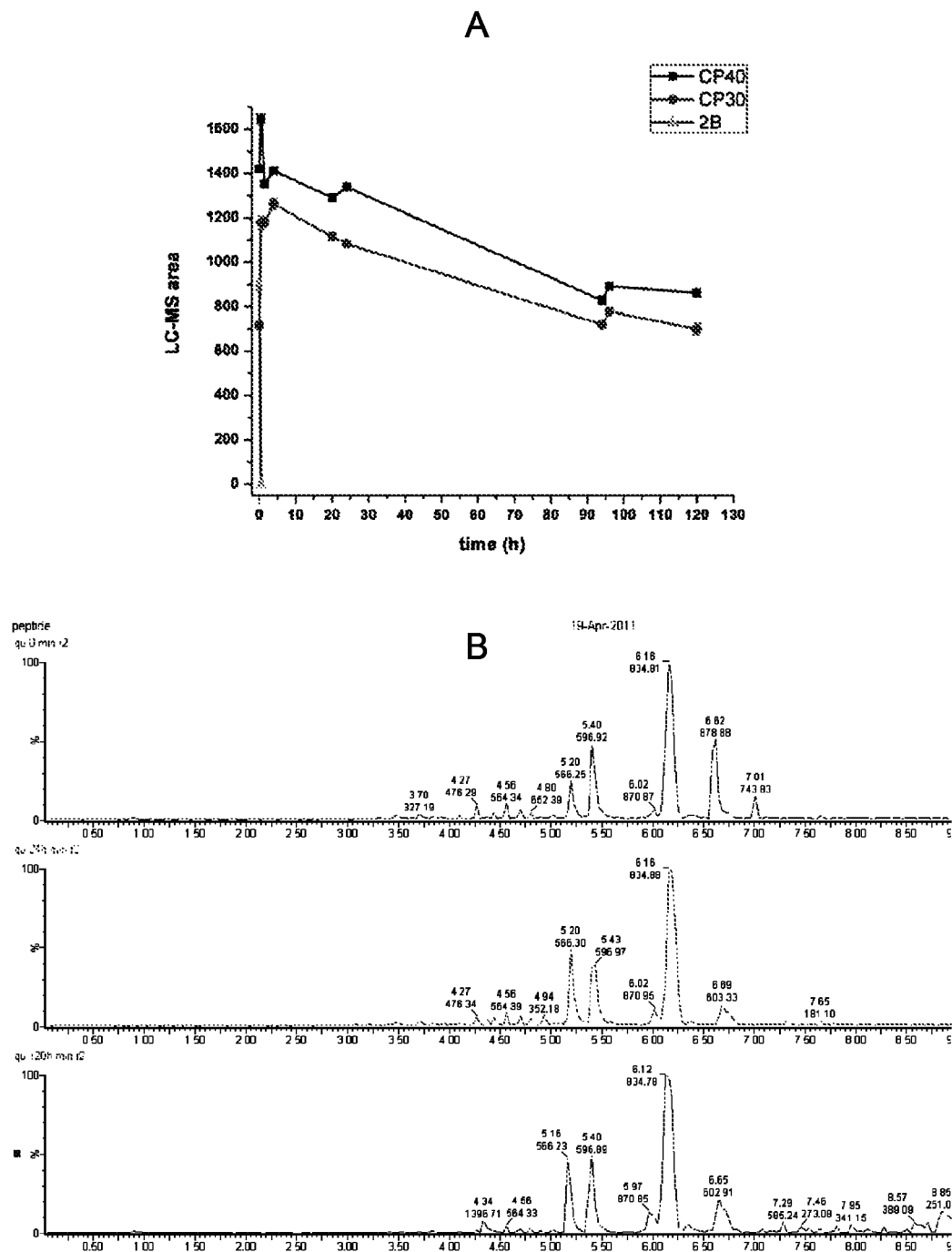
FIG. 4. Stability of peptide 3 (Cp30 (SEQ ID NO:7)) and peptide 14 (Cp40 (SEQ ID NO:18)) in human plasma at 37° C. Cp30 (SEQ ID NO:7), Cp40 (SEQ ID NO:18) and a positive control peptide 2B were spiked in human plasma to a reach a final concentration of 20 μM. The plasma was incubated at 37° C. and 100 μL of sample was taken at various time points. Peptides were extracted from plasma using solid phase extraction and analyzed using UPLC-MS. 4A: the area of each sample at different time point was plotted over time (square: Cp40 (SEQ ID NO:18), circle: Cp30 (SEQ ID NO:7), triangle: control peptide 2B). 4B: Chromatograph of samples from time 0 (Top), 24 h (middle) and 120 h (bottom).

To investigate the stability of the new analogs with free N-terminus, Cp30 (SEQ ID NO:7) and Cp40 (SEQ ID NO:18) were selected for incubation in human plasma at 37° C. (FIG. 4A). The control linear peptide 2B (LRFLN-PFSLDGSGFW, SEQ ID NO:28) was cleaved quickly upon contact with plasma. The zero time point sample showed cleavage at the Arg position. The peptide completely disappeared within 30 min. Under the same conditions, both Cp30 (SEQ ID NO:7) and Cp40 (SEQ ID NO:18) showed remarkable stability in plasma. More than 55% of peptides remain after 5 days. The UPLC-MS chromatograms at time 0, 24 and 120 h are quite similar (FIG. 4B). No major cleavage product was observed.

Plasma Protein Binding.

To investigate the binding specificity of Cp30 (SEQ ID NO:7), excessive peptide was incubated in fresh human plasma. Plasma proteins were precipitated with PEG3350 and separated using a small Mono Q column. Each 1 mL fraction was measured for the presence of Cp30 (SEQ ID NO:7). Fractions that contained Cp30 (SEQ ID NO:7) were further analyzed quantitatively using UPLC-MS and tested for the identity of the co-eluting protein. It was found that 7.5% of the Cp30 (SEQ ID NO:7) was located in the flow-through while 88.0% and 4.5% co-eluted with C3 and C3c, respectively. The identity of the proteins was identified by SDS-PAGE followed by Coomassie staining and Western Blot. In addition, the total amount of Cp30 (SEQ ID NO:7) detected was equal to the amount of plasma C3.

Example 5

Compstatin analogs Cp20 (SEQ ID NO:3), Cp30 (SEQ ID NO:7) and Cp40 (SEQ ID NO:18), synthesized as described in Example 1, were measured for in vivo retention in a cynomolgus monkey model. The binding profiles of the peptides were compared in plasma of four primate species: human, cynomolgus monkey, rhesus monkey and baboon, using the SPR method described above.

Materials and Methods:

Primate Studies and Sample Collection.

Evaluation of plasma half-life and generation of major metabolites was performed at the Simian Conservation Breeding and Research Center (SICONBREC, Makati City, Philippines) in cynomolgus monkeys (*Macaca fascicularis*). For each analog (Cp20 (SEQ ID NO:3), Cp30 (SEQ ID NO:7) and Cp40 (SEQ ID NO:18)), two healthy animals were sedated and injected intravenously with 2 mg/kg of the compound (dissolved in saline for injection). Blood samples (1-2 mL) were collected immediately before and at various time points after compound injection (2, 5 and 30 min; 1, 2, 4, 6, and 24 hours) in EDTA-coated Vacutainer tubes to prevent coagulation and complement activation, and centrifuged at ~800×g for 10 min to obtain plasma. Plasma samples were immediately frozen and stored for further analysis. All NHP studies were performed in accordance with animal welfare laws and regulations.

Analysis of Plasma Samples.

Prior to analysis by UPLC-MS, compstatin analogs in the plasma samples were extracted by solid phase extraction (SPE) in a 96-well plate format (HLB Oasis 30 µm, 10 mg; Waters, Milford, Mass.). The SPE material was thoroughly conditioned using acetonitrile and water. Plasma samples were diluted 1:1 with 4% phosphoric acid, and a constant concentration of Cp20 (SEQ ID NO:3) (5 µM) was spiked into all samples containing Cp30 (SEQ ID NO:7) or Cp40 (SEQ ID NO:18) as an internal standard; in the case of Cp20 (SEQ ID NO:3)-containing samples, Cp40 (SEQ ID NO:18) was used as internal standard. The samples were loaded on the SPE plate and washed with 10% acetonitrile in 0.1% formic acid. Extracted peptides were eluted with 200 µL of 65% acetonitrile in 0.1% formic acid and collected in a LoBind tube (Eppendorf) to avoid peptide adsorption. Finally, 5 µL of each eluent was diluted with 45 µL 0.1% formic acid and injected into the UPLC-MS system consisting of an online ACQUITY UPLC coupled to a SYNAPT G2-S HDMS instrument equipped with an ESI source and controlled by MassLynx 4.1 software (Waters). Each sample was injected in quadruplicates. Reversed-phase liquid chromatography was used for peptide separation with a 1.7 µM UPLC BEH130 C18 column (2.1 µm×150 mm; Waters) at a column temperature of 40° C. Peptides were separated at a flow rate of 0.15 mL/min with a linear gradient of 10-60% acetonitrile in water containing 0.1% formic acid over 8 min. Eluted peptides were directly analyzed by HDMS; the ESI source capillary voltage was set to 3.2 kV, the cone voltage to 30 V and the source temperature to 120° C. [Glu1]-fibrinopeptide B (Sigma) was used for lock-mass correction with a sampling rate of 30 s. Mass spectra were acquired in positive mode over an m/z range of 50-1950 Da at a scan rate of 1 s.

Determination of Plasma Half-Life.

Calibration curves were prepared on the day of the analysis by spiking compstatin analogs (Cp20 (SEQ ID NO:3), Cp30 (SEQ ID NO:7) and Cp40 (SEQ ID NO:18)) into freshly-thawed plasma from untreated cynomolgus monkeys at final concentrations of 0.5, 1, 2, 4, and 8 µM. All calibration samples were subjected to SPE and measured using UPLC-HDMS as described above. MS peak areas were determined by integration and plotted against the concentration, resulting in calibration curves that showed good linearity with regression coefficients (R2) greater than 0.993. For the pharmacokinetic analysis, the plasma concentration (Cp) at each time point was calculated from the extracted peak area of each peptide using the corresponding standard curve. The elimination constant ($k_e$) and plasma half-life ($t_{1/2}$) were determined from the slope of the terminal elimination phase (0.5-24 h) using the following equations: $\ln(Cp)=\ln(Cp0)-k_e \times t$, and $t_{1/2}=0.693/k_e$ Determination of C3 levels. The plasma concentration of C3 in individual cynomolgus monkeys used in this study was determined by ELISA. Briefly, 96-well plates (MaxiSorp; Nunc) were coated with 1 µg/ml of a monoclonal anti-C3 antibody (clone 8E11; Tosic et al., 1989, *J Immunol. Methods* 120: 241-249) in PBS overnight at 4.25° C. Wells were washed with PBS/Tween 0.05% and blocked with PBS/BSA 1% for 1 h at room temperature. Plasma (diluted 1:10,000 and 1:20,000 in PBS/BSA) or serial dilutions of purified cynomolgus monkey C3 were then incubated for 1 h at room temperature followed by washing and incubation with peroxidase-conjugated anti-C3 (MP Biomedicals, Solon, Ohio) diluted 1:1,000 in PBS/BSA for 1 h at room temperature. The reaction was developed using tetramethylbenzidine substrate (R&D Systems, Minneapolis, Minn.) per manufacturer's instructions and optical density was determined using a microplate reader with wavelength set at 450 nm.

Hemolytic Assay.

Rabbit erythrocytes were washed with phosphate-buffered saline (PBS) followed by washing with Veronal-buffered saline $(VBS)^{Mg+}$/EGTA. A 1:20 dilution was prepared in VBS buffer. Plasma samples (1:10 in VBS—100 µl) was incubated with the rabbit erythrocytes solution (50 µl) in a 96-well plate at 37° C. for 1 h. EDTA (0.2 mM-15 µl) was added to stop the reaction and plate was centrifuged (2500×g 3 min) Supernatant (100 µl) was transferred to a new well and optical density was measured at 405 nm. Incubation of erythrocytes with water or buffer was used as positive (100% lysis) and negative (0% lysis) control, respectively.

Binding Profiles.

For the NHP specificity experiments, C3 from human, cynomolgus monkey, rhesus monkey, and baboon plasma was immobilized on individual flow cells of CM5 sensor chips (GE Healthcare) using standard amine coupling to reach target densities of 6,000-7,000 RU. Peptides Cp20 (SEQ ID NO:3) and Cp40 (SEQ ID NO:18) were quantitatively evaluated using a single cycle kinetic approach as described in Example 2. To visually compare the kinetic profiles independently of differences in target density or activity, each binding curve was normalized to the maximum response and superimposed in Origin.

Figure 5:
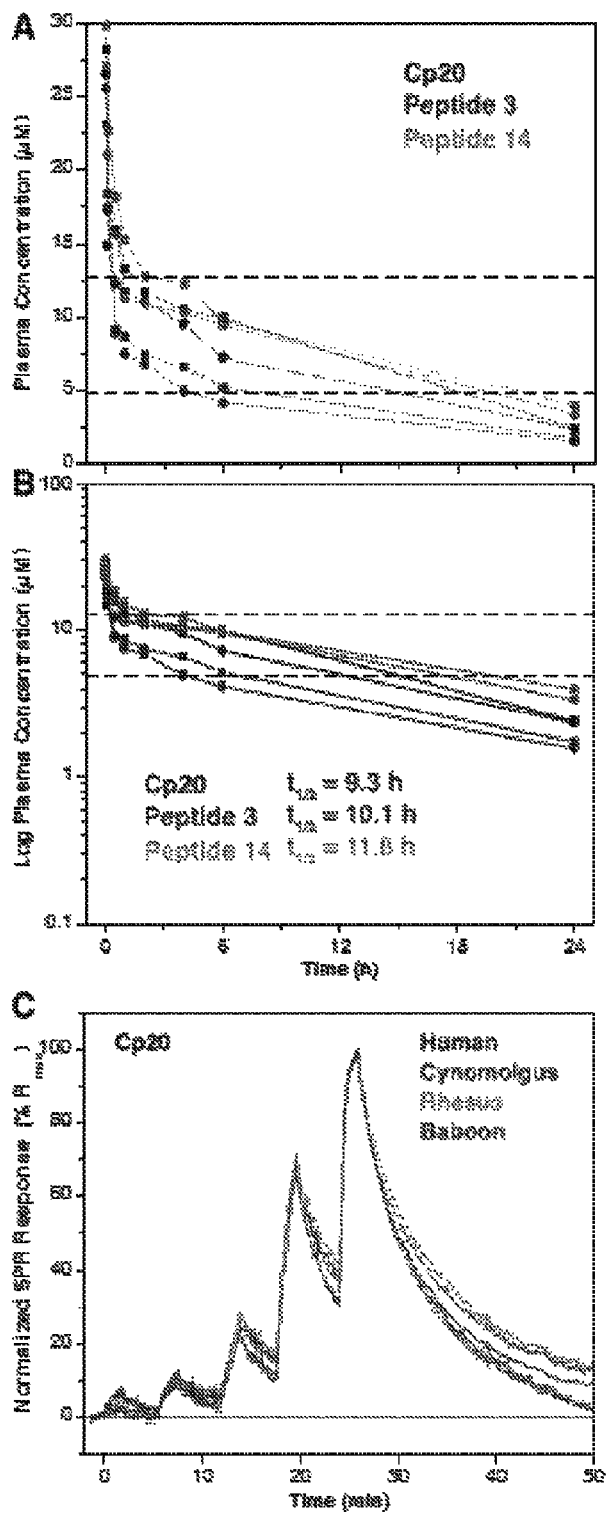
FIG. 5. Pharmacokinetic assessment of compstatin analogs in non-human primates. (A) Linear plot of peptide level over time after i.v. bolus injection of 2 mg/kg in cynomolgus monkeys, showing a biphasic model with a rapid initial elimination phase followed by a slow log-linear terminal phase. Cp20 (SEQ ID NO:3)—lower two lines; Cp30 (SEQ ID NO:7) (Peptide 3)—middle two lines; Cp40 (SEQ ID NO:18) (Peptide 14)—upper two lines. (B) Calculation of the plasma elimination half-life ($t_{1/2}$) from the terminal phase (1-24 h). Cp20 (SEQ ID NO:3)—lower two lines; Cp30 (SEQ ID NO:7) (Peptide 3)—middle two lines; Cp40 (SEQ ID NO:18) (Peptide 14)—upper two lines. Dashed lines mark the range of measured plasma levels of the target protein C3 in both panels A and B. (C) Superimposition of kinetic binding profiles of analog Cp20 (SEQ ID NO:3) to immobilized C3 from humans, baboons, cynomolgus monkeys and rhesus monkeys as assessed by SPR.

Results:

Peptidic drugs are often hampered by comparatively fast elimination from plasma, which may be highly restrictive in clinical applications that rely on constant systemic drug levels (e.g., PNH in the case of complement inhibitors). A comparative study including Cp20 (SEQ ID NO:3) and the newly developed Cp30 (SEQ ID NO:7) and Cp40 (SEQ ID NO:18) was performed, in which cynomolgus monkeys were intravenously injected with 2 mg/kg of each analog and the plasma levels were assessed by LC-MS over a period of 24 hours. All tested analogs followed a similar biphasic elimination profile, in which the plasma levels dropped more rapidly within the first hour after injection and then followed a much slower decrease throughout the later time points (FIG. 5A). The peptide concentrations at which the kinetic change occurred were very similar to that of the expected physiological plasma levels of the target protein C3. Indeed, measurement of the C3 levels in the involved monkeys by ELISA (4.9-12.8 µM) confirmed that the initial drop in compstatin levels slowed down within the determined range of C3 (FIG. 5A). These observations suggest a target-driven elimination model, where tight binding to the abundant target C3 largely influences peptide excretion. Indeed, when the plasma half-life was calculated based on the terminal log-linear portion (1-24 h), a direct correlation to the binding affinity for C3 could be observed with half-life values of 9.3, 10.1 and 11.8 h for Cp20 (SEQ ID NO:3), Cp30 (SEQ ID NO:7) and Cp40 (SEQ ID NO:18), respectively (FIG. 5B). The half-life of the Cp30-ABM2 conjugate was observed to be 22 hours (not shown).

Concentrations of compstatin analogs were measured against inhibition of complement activation via the alternative pathway in the plasma samples using an erythrocyte hemolytic assay. Complement inhibitory activity was observed to closely track the concentration of analog in the samples at each time point measured.

Given the strong apparent dependence of the major elimination phase with the binding affinity, the translation of these NHP-based studies to the human system appear to be influenced by the differential affinity of these compstatin analogs for human and NHP C3. Hence, the binding profiles of the peptides for C3 from humans and three relevant NHPs (cynomolgus monkey, rhesus monkey, baboon) was measured, using the SPR method described above. Both the affinity and kinetic profiles for all analogs were highly comparable (FIG. 5C).

Example 6

Compstatin analog Cp40 (SEQ ID NO:18), synthesized as described in Example 1, was measured for bioavailability from subcutaneous and oral routes of administration in a cynomolgus monkey model.

Materials and Methods:

Primate Studies and Sample Collection.

Evaluation of bioavailability was performed at the Simian Conservation Breeding and Research Center (SICONBREC, Makati City, Philippines) in cynomolgus monkeys (*Macaca fascicularis*). Two healthy animals were used for each route of administration. The animals were sedated and injected subcutaneously with 2 mg/kg of the compound or orally by intragastric gavage with 4 mg/kg of the compound. Blood samples (1-2 mL) were collected immediately before and at various time points after compound injection (2, 5 and 30 min; 1, 2, 4, 6, and 24 hours) in EDTA-coated Vacutainer tubes to prevent coagulation and complement activation, and centrifuged at ~800×g for 10 min to obtain plasma. Plasma samples were immediately frozen and stored for further analysis. All NHP studies were performed in accordance with animal welfare laws and regulations.

Analyses.

Analysis of plasma samples, determination of plasma half-life and complement inhibitory activity in plasma were performed as described in Example 5.

Results:

Peptidic drugs typically are very poorly bioavailable by any route except intravenous administration, which is expensive, not well tolerated by patients, and usually needs to be performed by a trained specialist. The compstatin analog Cp40 (SEQ ID NO:18) was tested for bioavailability following subcutaneous or oral delivery. Cynomolgus monkeys were subcutaneously injected with 2 mg/kg or orally injected with 4 mg/kg of the analog and the plasma levels were assessed by LC-MS over a period of 24 h. Results are shown in FIG. 6.

Figure 6:
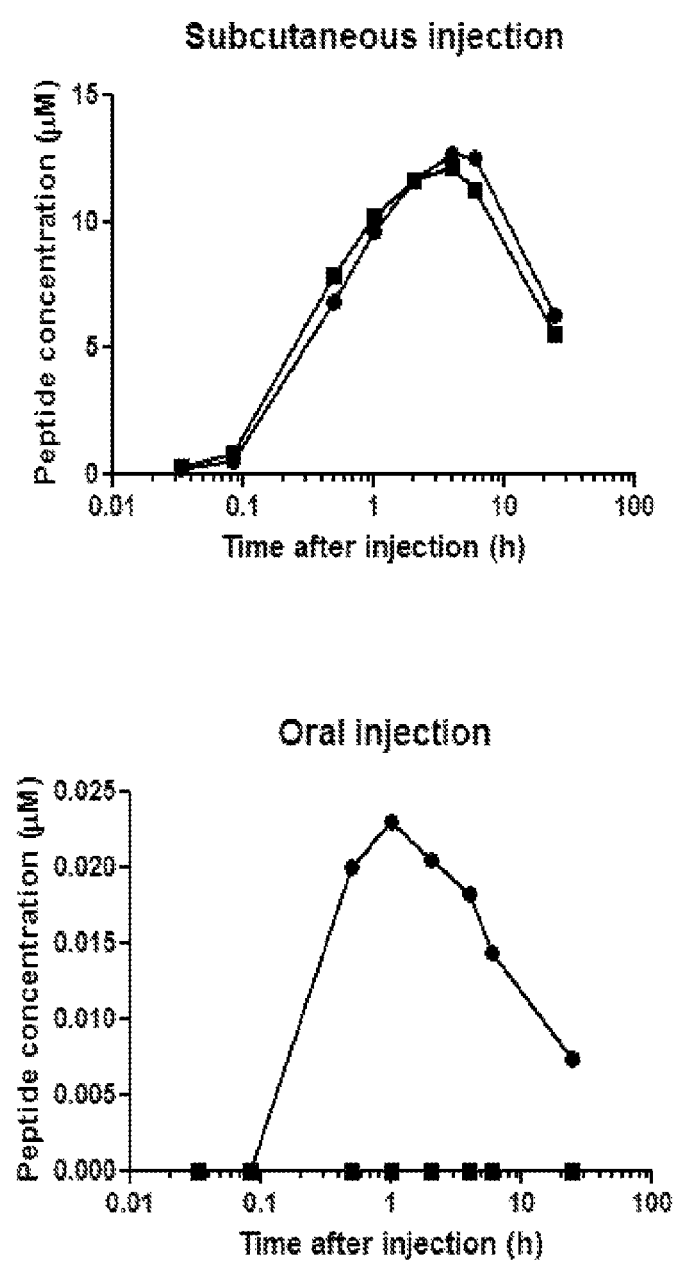
FIG. 6. Plasma concentrations of compstatin analogCp40 (SEQ ID NO:18) following a single administration of the analog by two different routes in cynomolgus monkeys. Plasma concentrations were measured by mass spectrometry at time points after subcutaneous injection (top panel) or oral administration (bottom panel).

The plasma concentration of Cp40 (SEQ ID NO:18) reached its peak of approximately 12.5 µM within 4-5 hours following administration by subcutaneous injection (FIG. 6, top panel). Oral injection of the analog resulted in a plasma concentration of approximately 0.023 µM within one hour of injection (FIG. 6, bottom panel; note the oral injection was successful on only one of the two monkeys). By comparison (FIG. 5B), intravenous injection of that analog resulted in peak plasma concentrations of approximately 28 µM immediately following injection.

Concentrations of Cp40 (SEQ ID NO:18) were measured against inhibition of complement activation via the alternative pathway in the plasma samples from the subcutaneous injection using an erythrocyte hemolytic assay. Complement inhibitory activity was observed to closely track the concentration of analog in the samples at each time point measured.

Example 7

Compstatin analog Cp30 (SEQ ID NO:7) and the Cp-30-ABM2 conjugate described in Example 1, were measured for in vivo retention in a baboon model.

Materials and Methods:

Juvenile baboons (*P. Anubis*, Baboon Research Resources, University of Oklahoma) weighing 5-8 kg were used. Two baboons were used for the study, one for each compound. Each animal received a bolus dose of peptide (10 mg) by injection through the peripheral vein. Blood samples for the LC-MS/MS assay were collected in 1-ml plastic tubes containing 50 µg lepirudin, and centrifuged at 2000 g for 20 min at 4° C. for plasma separation. Plasma samples were stored at −70° C. Blood samples were collected at pre-determined time intervals after injection of Cp30 (SEQ ID NO:7) or the Cp30 (SEQ ID NO:7)-ABM2 conjugate.

Samples were treated with SPE and analyzed using LC-MS/MS. Calibration curves were created using standard peptides at various concentrations in plasma to determine peptide concentration in each sample.

Extraction of Compstatin Analogs from Plasma Samples by SPE.

A 96-well plate HLB Oasis 30 μm 10 mg (Waters, Milford, Mass.) was employed for extraction. The SPE material was conditioned by addition of 500 μl of methanol, ACN followed by addition of 500 μL of milli-Q water. Samples were diluted with 4% $H_3PO_4$. After loading a sample, washing was carried out with 500 μL of water and 10% ACN with 0.1% formic acid. Samples were eluted with 200 μL of 65% ACN in 0.1% formic acid and collected in the collection plate. Samples for LC-MS were diluted 1:2 to 1:11 in milli-Q water with 10% ACN with 0.1% formic acid. CP20 (SEQ ID NO:3) was spiked in each sample before SPE, as an internal standard.

LC-MS/MS Analysis.

LC-MS/MS analysis was performed on a SYNAPT HDMS (Waters, Milford, Mass.) equipped with an ESI source controlled by MassLynx 4.1 software (Waters). Each sample was injected in triplicate. An online ACQUITY UPLC (Waters) system was used for peptide separation by reversed-phase liquid chromatography. The capillary voltage was 3.2 kV, the cone voltage was 30 V and the source temperature was 120° C. [Glu1]-fibrinogen peptide was used for lock-mass correction with a sampling rate of 30 s. Mass spectra were acquired in positive mode over an m/z range 500-1800 Da at scan rate of is. The presence of the analyte was confirmed by retention time and mass. After injection, analytes were separated on a 1.7 μm UPLC BEH130 C18 column (Water, 1.0 μm×100 mm). The analytical column temperature was held at 40° C. Peptides were separated at flow rate 0.15 mL/min. The gradient was linear 15-55% B (0.1% formic acid in acetonitrile) over 7 min.

Results:

The plasma concentrations of peptide Cp30 (SEQ ID NO:7) and the ABM2 conjugate were determined using LC-MS/MS after an intravenous bolus injection into baboons. Peptide Cp30 (SEQ ID NO:7) displayed a half-life of 5 hours and Cp30 (SEQ ID NO:7)-ABM2 displayed a half-life of 7.5 hr. By comparison, in the same baboon model, compstatin analog 4 (1 MeW) and a potent analog (peptide 3) disclosed in WO2010/127336 were previously determined to have half-lives of approximately 60-90 minutes.

Example 8

Compstatin analog Cp40 (SEQ ID NO:18), synthesized as described in Example 1, was measured for bioavailability from an intramuscular route administration in a baboon model.

Methods:

A juvenile baboon was injected intramuscularly with 2 mg/kg Cp40 (SEQ ID NO:18) Blood samples for the LC-MS/MS assay were collected in 1-ml plastic tubes containing 50 μg lepirudin, and centrifuged at 2000 g for 20 min at 4° C. for plasma separation. Plasma samples were stored at −70° C. Blood samples were collected at pre-determined time intervals after injection of the analog. Samples were treated with SPE and analyzed using LC-MS/MS. Calibration curves were created using standard peptides at various concentrations in plasma to determine peptide concentration in each sample.

Extraction of compstatin analog from plasma samples and LC-MS/MS analysis were performed as described in Example 7. A hemolytic assay was performed as described in Example 5.

Figure 7:
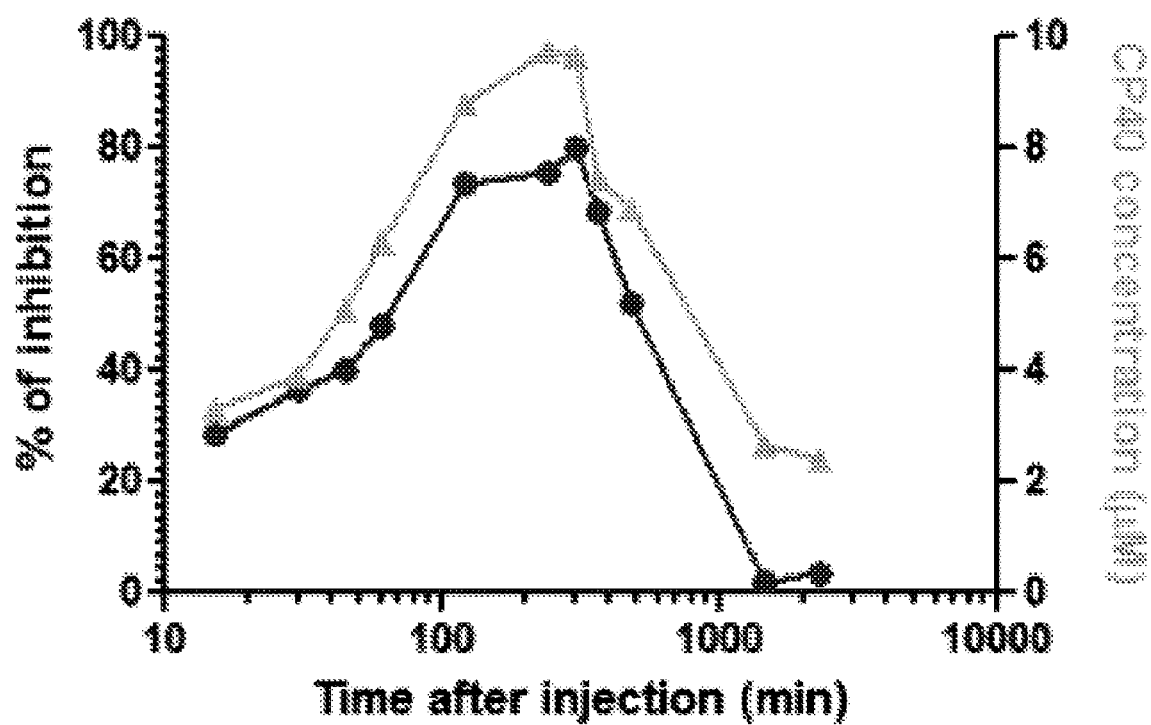
FIG. 7. Plasma concentrations and complement inhibitory activity of compstatin analogCp40 (SEQ ID NO:18) following a single administration of the analog by intramuscular injection in a baboon. Plasma concentrations were measured by mass spectrometry at time points after intramuscular injection (circles). Inhibition of complement activation via the alternative pathway was measured by an erythrocyte hemolytic assay (triangles).

Results:

Results are shown in FIG. 7. The plasma concentration of Cp40 (SEQ ID NO:18) reached its peak of approximately 10 μM within about 5-6 hours following administration by intramuscular injection. Complement inhibitory activity was observed to closely track the concentration of analog in the samples at each time point measured.

The present invention is not limited to the embodiments described and exemplified above, but is capable of variation and modification within the scope of the appended claims.

What is claimed:

1. A compound comprising a peptide having a sequence of SEQ ID NO:29, which is:

Xaa1-Xaa2-Cys-Val-Xaa3-Gln-Xaa4-Xaa5-Gly-Xaa6-His-Xaa7-Cys-Xaa8, in which Gly between Xaa5 and Xaa6 optionally is modified to constrain the backbone conformation;

wherein:

Xaa1 is absent or is selected from the group consisting of D-Tyr, D-Phe, Tyr(Me), D-Trp, D-Cha, Cha, Phe, Sar, Arg, mPhe, mVal, Trp, mIle, D-Ala, mAla, Thr or Tyr;

Xaa2 is Ile when Xaa1 is D-Tyr, D-Phe, Tyr(Me), D-Trp, D-Cha, Cha, Phe, Sar, Arg, mPhe, mVal, Trp, mIle, D-Ala, mAla or Thr, or either Ile or Gly when Xaa1 is Tyr, or Ac-Trp when Xaa1 is absent;

Xaa3 is Trp or an analog of Trp, wherein the analog of Trp has increased hydrophobic character as compared with Trp;

Xaa4 is Asp;

Xaa5 is Trp or an analog of Trp comprising a chemical modification to its indole ring wherein the chemical modification increases the hydrogen bond potential of the indole ring;

Xaa6 is His, Ala, Phe or Trp;

Xaa7 is Arg; and

Xaa8 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$, and the peptide is cyclic via a Cys-Cys disulfide or thioether bond.

2. The compound of claim 1, wherein:

the Gly at position 8 is N-methylated;

Xaa1 is D-Tyr or Sar;

Xaa2 is Ile;

Xaa3 is Trp, 1-methyl-Trp or 1-formyl-Trp;

Xaa5 is Trp or halogenated Trp;

Xaa6 is Ala; and

Xaa8 is Thr, Ile, Leu, Nle, N-methyl Thr or N-methyl Ile with optional replacement of the carboxy terminal —OH with —NH$_2$.

3. The compound of claim 2, wherein Xaa8 is Ile, N-methyl Thr or N-methyl Ile with optional replacement of the carboxy terminal —OH with —NH$_2$.

4. The compound of claim 3, which comprises SEQ ID NO:7 or SEQ ID NO:18.

5. The compound of claim 1, further comprising an additional component that extends the in vivo retention of the compound.

6. The compound of claim 5, wherein the additional component is selected from:

(a) polyethylene glycol (PEG);

(b) an albumin binding small molecule; and (c) an albumin binding peptide.

7. The compound of claim 6, wherein the albumin binding small molecule is attached to a terminus of the peptide, either directly or with a spacer between the peptide and the albumin binding small molecule.

8. The compound of claim 1, disposed within a pharmaceutical composition comprising a pharmaceutically acceptable carrier for the compound.

9. A compound comprising a peptide having a sequence of SEQ ID NO:29, which is:

Xaa1-Xaa2-Cys-Val-Xaa3-Gln-Xaa4-Xaa5-Gly-Xaa6-His-Xaa7-Cys-Xaa8, in which Gly between Xaa5 and Xaa6 optionally is modified to constrain the backbone conformation;

wherein:

Xaa1 is absent or is selected from the group consisting of D-Tyr, D-Phe, Tyr(Me), D-Trp, D-Cha, Cha, Phe, Sar, Arg, mPhe, mVal, Trp, mIle, D-Ala, mAla, Thr or Tyr;

Xaa2 is Ile when Xaa1 is D-Tyr, D-Phe, Tyr(Me), D-Trp, D-Cha, Cha, Phe, Sar, Arg, mPhe, mVal, Trp, mIle, D-Ala, mAla or Thr, or either Ile or Gly when Xaa1 is Tyr, or Ac-Trp when Xaa1 is absent;

Xaa3 is Trp or an analog of Trp, wherein the analog of Trp has increased hydrophobic character as compared with Trp;

Xaa4 is Asn;

Xaa5 is Trp or an analog of Trp comprising a chemical modification to its indole ring wherein the chemical modification increases the hydrogen bond potential of the indole ring;

Xaa6 is His, Ala, Phe or Trp;
Xaa7 is Arg or Orn; and
Xaa8 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$, and
the peptide is cyclic via a Cys-Cys disulfide or thioether bond.

10. The compound of claim 9, wherein:
the Gly at position 8 is N-methylated;
Xaa1 is D-Tyr or Sar;
Xaa2 is Ile;
Xaa3 is Trp, 1-methyl-Trp or 1-formyl-Trp;
Xaa5 is Trp or halogenated Trp;
Xaa6 is Ala; and
Xaa8 is Thr, Ile, Leu, Nle, N-methyl Thr or N-methyl Ile with optional replacement of the carboxy terminal —OH with —NH$_2$.

11. The compound of claim 9, further comprising an additional component that extends the in vivo retention of the compound.

12. The compound of claim 11, wherein the additional component is selected from:
(a) polyethylene glycol (PEG);
(b) an albumin binding small molecule; and
(c) an albumin binding peptide.

13. The compound of claim 12, wherein the albumin binding small molecule is attached to a terminus of the peptide, either directly or with a spacer between the peptide and the albumin binding small molecule.

14. The compound of claim 9, disposed within a pharmaceutical composition comprising a pharmaceutically acceptable carrier for the compound.

15. A compound comprising a peptide having a sequence of SEQ ID NO:29, which is:
Xaa1-Xaa2-Cys-Val-Xaa3-Gln-Xaa4-Xaa5-Gly-Xaa6-His-Xaa7-Cys-Xaa8, in which Gly between Xaa5 and Xaa6 optionally is modified to constrain the backbone conformation;
wherein:
Xaa1 is absent or is selected from the group consisting of D-Tyr, D-Phe, Tyr(Me), D-Trp, D-Cha, Cha, Phe, Sar, Arg, mPhe, mVal, Trp, mIle, D-Ala, mAla, Thr or Tyr;
Xaa2 is Ile when Xaa1 is D-Tyr, D-Phe, Tyr(Me), D-Trp, D-Cha, Cha, Phe, Sar, Arg, mPhe, mVal, Trp, mIle, D-Ala, mAla or Thr, or either Ile or Gly when Xaa1 is Tyr, or Ac-Trp when Xaa1 is absent;
Xaa3 is Trp or an analog of Trp, wherein the analog of Trp has increased hydrophobic character as compared with Trp;
Xaa4 is Asp or Asn;
Xaa5 is Trp or an analog of Trp comprising a chemical modification to its indole ring wherein the chemical modification increases the hydrogen bond potential of the indole ring;
Xaa6 is His, Ala, Phe or Trp;
Xaa7 is Orn; and
Xaa8 is Thr, Ile, Leu, Nle, N-methyl Thr or N-methyl Ile, wherein a carboxy terminal —OH of any of the Thr, Ile, Leu, Nle, N-methyl Thr or N-methyl Ile optionally is replaced by —NH$_2$, and
the peptide is cyclic via a Cys-Cys disulfide or thioether bond.

16. The compound of claim 15, wherein:
the Gly at position 8 is N-methylated;
Xaa1 is D-Tyr or Sar;
Xaa2 is Ile;
Xaa3 is Trp, 1-methyl-Trp or 1-formyl-Trp;
Xaa5 is Trp or halogenated Trp;
Xaa6 is Ala; and
Xaa8 is Thr, Ile, Leu, Nle, N-methyl Thr or N-methyl Ile with optional replacement of the carboxy terminal —OH with —NH$_2$.

17. The compound of claim 15, further comprising an additional component that extends the in vivo retention of the compound.

18. The compound of claim 17, wherein the additional component is selected from:
(a) polyethylene glycol (PEG);
(b) an albumin binding small molecule; and
(c) an albumin binding peptide.

19. The compound of claim 18, wherein the albumin binding small molecule is attached to a terminus of the peptide, either directly or with a spacer between the peptide and the albumin binding small molecule.

20. The compound of claim 15, disposed within a pharmaceutical composition comprising a pharmaceutically acceptable carrier for the compound.

* * * * *